(12) United States Patent
Fontaine et al.

(10) Patent No.: US 6,551,811 B1
(45) Date of Patent: Apr. 22, 2003

(54) METHOD FOR SORTING ANTIFUNGAL MOLECULES ACTING ON THE GLUCANOSYLTRANSFERASE ACTIVITY

(75) Inventors: Thierry Fontaine, Issy les Moulineaux (FR); Robbert Hartland, Darlington (AU); Isabelle Mouyna, Paris (FR); Jean-Paul Latge, Issy les Moulineaux (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 09/242,913

(22) PCT Filed: Aug. 29, 1997

(86) PCT No.: PCT/FR97/01540

§ 371 (c)(1),
(2), (4) Date: Oct. 13, 1999

(87) PCT Pub. No.: WO98/08937

PCT Pub. Date: Mar. 5, 1998

Related U.S. Application Data

(60) Provisional application No. 60/024,910, filed on Aug. 30, 1996.

(51) Int. Cl.$^7$ .......................... C12N 9/24; C07K 14/195
(52) U.S. Cl. ...................................... 435/200; 530/350
(58) Field of Search ...................... 435/4, 200; 530/350

(56) References Cited

PUBLICATIONS

Hartland et al. A secreted beta–glucan–branching enzyme from Candida albicans. Proc. R. Soc. Lond. B vol. 246:155–160, 1991.*

Nouffer et al. Determinants fro glycophospholipid anchoring on the Sacharomyces cerevisiae GAS1 protein to the plasma membrane. Mol. and Cellular Biol. vol. 11(1):27–37, 1991.*

Yu et al. Heteronuclear NMR studies of C–13 labeled yeast cell wall beta glucan oligosaccharides. J. Biomolecular NMR. vol. 3:429–441, 1993.*

Mittendorf et al. Cloning of an endo–1–4–beta–glucanase gene celA, from the rumen bacterium Clostridium sp. (C. longisporum) and characterization of its product, CelA, in Esherichia coli. J. Gen Microbiol. vol. 139:3233–3242, 1993.*

Pazur et al. The isolation and mode of action of a bacterial glucanosyltransferase. J. Biol. Chem. vol. 243(18):4732–4738, 1968.*

R. Hartland et al., "A Novel β–(1–3)–Glucanosyltransferase from the Cell Wall of *Aspergillus fumigatus*", J. Biol. Chem., 271(43) :26843–26849, (1996).

M. Rad et al., "Analysis of the DNA Sequence of a Region on the Left Arm of Yeast Chromosome XV", Yeast, 13:281–286, (1997).

C. Nuoffer et al., "Determinants for Glycophospholipid Anchoring of the *Saccharomyces cerevisiae* GAS1 Protein to the Plasma Membrane", Mol. Cell. Biol., 11(1):27–37, (1991).

S. Saporito–Irwin et al., "PHR1, a pH–Regulated Gene of *Candida albicans*, Is Required for Morphogenesis", Mol. Cell. Biol., 15(2) :601–613, (1995).

R. Hartland et al., "A Secreted β–glucan–branching enzyme from *Candida albicans*", Proc. R. Soc. Lond. B, 246:155–160, (1991).

* cited by examiner

Primary Examiner—Terry McKelvey
Assistant Examiner—William Sandals
(74) Attorney, Agent, or Firm—Finnegan, Henderson, Farabow, Garrett & Dunner, L.L.P.

(57) ABSTRACT

The invention discloses proteins having β(1-3) glucanosyltransferase type activities. These proteins can be used for detecting the antifungal activity of molecules.

8 Claims, 13 Drawing Sheets

```
S  ..MLFKSLSKLATAA....AFFAGVAT..ADDVPAIEVVGNKFFYSNNGSQFYIRGVAYQ
C  MYSLIKSLATFATFA....TLFSLTLAKFESSTPPVEVVGNKFYFSNNGSQFLIRGIAYQ
A  ....MKASAVTAALAVGASTVLAAPSIKARDDVTPITVKGNAFF..KGDERFYIRGVDYQ

S  ADIANETSGS.......TVNDPLANYESCSRDIPYLKKLNTNVIRVYAINTTLDHSECMK
C  QDAAGSVSSGYDADPNRKYNDPLADRDACKRDVKYFKESNTNTLRVYAIDPDKDHEECMK
A  PGGSSD...........LADEIADADGCKRDIAKFKELGLNTIRVYSVDNSKNHDECMN

S  ALNDADIYVIADLAAPATSINRDDP.TWTVDLFNSYK.TVVDTFANYINVLGFFAGNEVT
C  IFSDAGIYIVADLSEPTVSINRNNP.EWNLDLYKRYT.KVIIDKMQEYSNVLGFFAGNEVT
A  TLADAGIYLVLDVNTEKYSINRAKPKESYNDVYLQYIFATVDAFAGYKNTLAFFSGNEVI

S  NNYINTDASAFVKAAIRDVRQYISDKNYRKIPVGYSS.................NDD
C  NNRSNTDASAFVKAAIRDMKKYIKESDYRQIPVGYSS.................NDD
A  NDGPSSSAAPYVKAVTRDLRQYIRSRKYREIPVGYSAVSSSATSW*FVTSC*LVHT*ADI
                                          ←――――――――――――→
                                                I₁

S  EDTRVKMIDYFACGDDDVKADFYGINMYEWCGKSDFKTSGYADRTAEFKNLSIPVFFSEY
C  EEIRVAIADYFSCGSLDDRADFFGINMYEWCGKSTFETSGYKDRTEEIKNLTIPAFFSEY
A  DTNRLQMAQYMNCGSDDERSDFFAFNDYSWCDPSSFKTSGWDQKVKNFTGYGLPLFLSEY

S  GCNEVTPRLFIEVEALYGSNMTDVWSGGIVYMYFEEINKYGLVSIDGNDVKTLDDFNNYS
C  GCNANRPRLFQEIGTLYSDKMTDVWSGGIVYMYFEEANKYGLVLVDGNSVKTLSDYNNYK
A  GCNINK.RQFQEVSSLYSTDMTGVYSGGLVYEYSQEASNYGLVPISGNNVKELPDFDALK

S  SEINKISPTSANTK..SYSAITSDVACPAT.GKYWSAATELPPTPNGGLCSCMNAANSCV
C  SEMNKISPSLAHTSTLSSSDASKTLQCPGTAASTWKAATNLPPTPDESYCDCISKSLPCV
A  TAFEKTSNPSGDGN...YNKTGGANPCPAKDAPNWDVD.......NDALPAIPEPAKKYM

S  VSDDVDSDDYETLFNWICNEVDCSGISANGTAGKYGAYSFCTPKEQLSFVMNLYYEKSGG
C  VADDVDKEDYGDLFGQVCGYIDCSAISADGSKGFYGVASFCSDKDRLSYVLNQYYLDQDK
A  TEGAGKGPGFA.................................................

S  SKSDCSFSGSATLQTATTQASCSSALKEIGSMGTNSASGSVDLGSGTESSTASSNASGSS
C  KSSACDFKGSASIN...SKASASGSCKAVSGVATGKAS.....SSGGSSKSGSSSASASG
A  .........................................GPGSQDRGTQSTATAEPGSGSATGSS

S  SKSNSGSSGSSSSSSSSSSKKNAATNVKANLAQVVFTSIISLFIAAGVGFALV.
C  SSSSSTSSGSSSSS........GVKATQQMSMVKLVSIITIVTAFVGGMSVVF
A  SSGTSTSSKGAAAGL........IVPSLIMAPVVVGAVTLLSTVFGAGLVLL*
```

FIG. 7

```
         1                                                                  50
SEQ ID NO:15   Gas3p   .........   .....MQLSK   SILLAALAAT   PSLVNAMLPI   HIKNYRFIKP
SEQ ID NO:16   Gas5p   .........   .....MMVFSS   TFIFLILELV   VLCEASVHTI   QIKDKHFVDT
SEQ ID NO:2    A       ......MK    ASAVTAALAV   GASTVLAAPS   IKARDDVTPI   TVKGNAFFKG
SEQ ID NO:17   Gas4p   .......ML   LRSLTSAFVL   SAGLAQAASS   ..SNSSTPSI   EIKGNAFFNS
SEQ ID NO:18   Gas2p   ...MNKKQNF  YAAIVAIFL    CLQLSHGSSG   V.SFEKTPAI   KIVGNKFFDS
SEQ ID NO:19   PHR1    MYSLIKSLAT  FATF..ATLF   SLTLAKFESS   ......TPPV   EVVGNKFYFS 51                                                                 100
Gas3p   SSATNSESDN   EVFFVKGVDY   QPGGSSGYDA   DSD.......   TDILSDPEVC
Gas5p   VTG.......   KPFFIKGVDY   QPGGSS..DV   SEK.......   QDPLSNPDAC
A       D.........   ERFYIRGVDY   QPGGSSD...   .........L   ADPLADADGC
Gas4p   ESG.......   ERFYIRGVDY   QPGGSSN...   .........L   TDPLADASVC
Gas2p   ESG.......   EQFFIKGIAY   QLQRSEEELS   NANGAFETSY   IDALADPKIC
PHR1    NNG.......   SQFLIRGLAY   QQDAAGSVSS   GYDADPNRKY   NDPLADRDAC 101                                                                150
Gas3p   ARDAYAFQQL   GVNTVRIYSL   NPDLNHDKCM   TIFNNAGIYA   ILDVNSGNYG
Gas5p   ARDILLFQEL   GINTVRIYSI   NPDLNHDACM   TMLAMAGIYL   ILDVNSPLQN
A       KRDIAKFKEL   GLNTIRVYSV   DNSKNHDECM   NTLADAGIYL   VLDVNTP..K
Gas4p   DRDVPVLKDL   GINTVRVYTV   DNSQDHSHCM   KLLQENGIYL   ILDVNTP..T
Gas2p   LRDIPFLKML   GVNTLRVYAI   DPTKSHDICM   EALSAEGMYV   LLDLSEP..D
PHR1    KRDVKYFKES   NINTLRVYKES NNTLRVYKES   NNTLRVYKES   NNTLRVYKES
```

```
       201                                                      250
Gas3p  KIDPPYIRAV QRDMKQYISK HANRSIPVGY SA..................
Gas5p  QYSPAYVKEL IGTMQNYISA HSPRTIPVGY SA..................
A      SSAAPYVKAV TRDLRQYIRS RKYREIPVGY SA..................
Gas4p  TNTATYVKAV VRDMKYIKA  RKYRQIPVGY SA..................
Gas2p  TFASPFVKAA IRDAKEYISH SNHRKIPVGY ST..................
PHR1   TDASAFVKAA IRDMKKYIKE SDYRQIPVGY SS..................

251                                                      300
Gas3p  ..ADNTDLRL ATFKYLQCNS LDGNKVNDDL DISKSDFFGL NTYEWCSGTS
Gas5p  ..ADDLNYRV SLSEYLECK. ........DDDK PENSVDFYGV NSYQWC.GQQ
A      ..ADIDTNRL QMAQYMNC.. .......GSD .DERSDFFAF NDYSWC.DPS
Gas4p  ..ADIVANRQ LAAEYFNC.. .......GDE ADARIDMFGV NDYSWC.GES
Gas2p  ..NDDAMTRD NLARYFVC.. .......G... .DVKADFYGI NMYEWC.GYS
PHR1   ..NDDEEIRV AIADYFSC.. .......GS. LDDRADFFGI NMYEWC.GKS 301                                                      350
Gas3p  SWESSGYDKL NSTFEDAVIP LIFSEYGCNK N.TPRTFDEV SEGLYGGLKN
Gas5p  TMQTSGYDTL VDAYRSYSKP VFFSEFGCNK V.LPRQFQEI GYLFSEEMYS
A      SFKTSGWDQK VKNFTGYGLP LFLSEYGCNT NK..RQFQEV SSLYSTDMIG
Gas4p  SFVVSGYSTK MKLYQDYSVP VFLSEFGCNQ VKSSRPFTEI EAIYSTQMSS
Gas2p  TYGTSGYRER TKEFEGYPIP VFFSEFGCNL VR.PRPFTEV SALYGNKMSS
PHR1   TFETSGYKDR TEEIKNLTIP AFFSEYGCNA NR.PRLFQEI GTLYSDKMTD
                             <---P4--->

351                                                      400
Gas3p  VFSGGLVYEY TEEANNYGLV KLDDSGSLTY KDDFVNLESQ LKNVSLPITK
Gas5p  VFCGGLVYEF SQEDNNYGLV EYQEDDSVQL LADFEKLKSH YQNIEFPSMK
A      VYSGGLVYEY SQEASNYGLV EISGNN.VKE LPDFDALKTA FEKTSNPS.G
Gas4p  VFSGGLVYEY SNETNNYGLV QIDGDK.VTK LTDFENLKNE YSKVSNPE.G
Gas2p  VWSGGLAYMY FEEENEYGVV KINDNDGVDI LPDFKNLKKE FAKADPKGIT
PHR1   VWSGGIVYMY FEEANKYGLV LVDGN.SVKT LSDYNNYKSE MNKISP.SLA 401                                                      450
Gas3p  ESEISSDS.. ..IYKCDNSA ITNIYSGFGT NNFTLPSQPA .......E..IA
Gas5p  TLK..ET... ..VQMEETPS CAEDY..... ENLKIESKIA ......KNLGS
A      DGNYNKTGA  N......PCPA KDAPNWDVDN DALPAIPEPA KKYMTEGAG.
Gas4p  NGGYSTSNNY S......TCPD YEKGVWE.AN NTLPAMPSAA SAYFTSGAGS
Gas2p  EEEYLTAKEP TEVESVECPH IAVGWEANE KLPETPDRSK CACLDEILPC
PHR1   HTSTLSSSDA S..KTLQCPG TAASTWKAAT NLPPTPDESY CDCISKSLEC
```

FIG. 10B

```
        451
Gas3p   NMIEYGVNGT NTGKILTDYA VPTTFNYTIK NNKDDTISAT ISYDKANSL.
Gas5p   SLIKKGVK.V EKGKYIDIHE DQLSTNVTIL DKHGDRWNGP KKIEIRQSL.
A       .KGPGFAGPG .......... .......S.. ...QDRGT.. ..........
Gas4p   PMGTGIATQQ .......... .......... ...SCDAKD  DDDEED....
Gas2p   EIVPFGAESG KYEEYFSYLC SKVDCSDILA NGKTGEYGEF SDCSVEQKLS
PHR1    .VVADDVDKE DYGDLFGQVC GYIDCSAISA DGSKGEYGVA SFCSDKDRLS 501                                                 550
Gas3p   .......... .......... .......... .NELD VTATTVAKSA STSQSSSRSL
Gas5p   .......... .......... .......... ....TLAD LEGEEQEDAD EDKDDLKRKH
A       .......... .......... .......... ...QS TATAEPGSGS ATGSSSSGTS
Gas4p   .......... .......... .......... ...DD TSSSSSSSS  SSSASSSE
Gas2p   LQLSKLYCKI GANDRHCPLN DKNVYFNLES LQPLTSES.I CKNVFDSIRN
PHR1    YVLNQYYLDQ DKKSSACDFK GS........AS INSKASASGS CKAVSGVATG 551                                                 600
Gas3p   TSSTSPSSST GSSSSTGSSS ASSSSKSKGV GNIVNVSFSQ SGYLALFAGL
Gas5p   RNSASIS... .......... .......... GPLLPLGL.. ..CLLFFT..
A       TSSKGAAAGL TVPSLTMAPV VVGAVTLLS. .......... .TVFGAGLVL
Gas4p   SSSSTSKASS SSPSASETSL LKSAASATSS SQSSSKSKGA AGIIEIPLIF
Gas2p   ITYNHGDYSK SNPSRSKESL NVKYPSSEER ENDGTIAFKT SGFVLLISM
PHR1    KASSSGGSSK SGSSSASASG SSSSSTSSGS SSSSGVKATQ QMSMVKLVSI 601    615
Gas3p   ISALL..... .....
Gas5p   FSLFF..... .....
A       L*........ .....
Gas4p   RALAELYNLV L....
Gas2p   IAAGILL... .....
PHR1    ITIVTAFVGG MSVVF
```

FIG. 10C

METHOD FOR SORTING ANTIFUNGAL MOLECULES ACTING ON THE GLUCANOSYLTRANSFERASE ACTIVITY

This application claims the benefit of Ser. No. 60/024,910, filed Aug. 30, 1996.

This invention relates to a protein with an activity of the glucanosyltransferase type, and more especially a β-(1-3)-glucanosyltransferase activity.

This invention also relates to oligonucleotides coding for this protein having an enzymatic activity.

It also relates to molecules having an effect on the activity of this enzyme.

Opportunistic fungal infections due to Candida, Aspergillus, Cryptococcus and Pneumocystis are responsible for the increase in morbidity and mortality among patients suffering from AIDS and other patients with clinically compromised immunity. In addition, the yeast Candida and the dermatophytes today remain a major medical problem amongst patients with adequate immunity, Despite the increase in the number of infections due to pathogenic and opportunistic fungi, therapy against mycoses has not improved in recent years. Two families of drugs are used: the azoles and Amphotericin B. These drugs have some disadvantages since treatment based on Amphotericin B is associated with nephrotoxicity and that based on azole is more fungistatic than fungicidal.

Fungi are microorganisms of the eukaryotic type which share the majority of their biochemical pathways with their hosts, with one important exception: the biosynthesis of the cell wall. The cell wall is a rigid envelope which protects the cell against the environment and mechanical stresses, but is also a dynamic structure which is involved in the transport of ions and macromolecules and in the localization of enzymes involved in fungal growth. In consequence, disorganization of the organization of the cell wall should be detrimental to fungi.

The skeleton of the fungal cell wall is mainly composed of polymers of the polysaccharide type (β(1-3) glucans, mannans, chitin) which are not found in humans. For this reason, the biosynthesis of the cell wall has been a target for research into new antifungal drugs. The penicillins and cephalosporins, which are both inhibitors of the bacterial cell wall, and potential antibiotics lend support to this hypothesis. Moreover, many molecules which inhibit the development of the fungal cell wall have antifungal properties (Debono and Gordee, 1994, Annu. Rev. Microbiol, 48, 471–497). Among these are:

1) The families of the echinocandin lipopeptides and the palulacandin glycopeptides which are non-competitive inhibitors of the glucan synthetase complex.

2) The polyoxins and nikkomycins which are analogs of UDP-GlcNac and potential competitive inhibitors of chitin synthetase, and 3) The pradimycins binding mannan and the benanomycins.

The synthesis of β(1-3) glucan and chitin is under the control of enzyme complexes (glucan synthetase and chitin synthetase) which are localized in the plasma membrane. Once the polymers have been released into the periplasmic space, cross-links are created between the polymers and it is these which are responsible for the rigidity of the cell wall. The proteins and genes of the glucan and chitin synthetases are beginning to be fairly well understood.

However, the inhibition of the glucan and chitin synthetases by a molecule requires three steps: its transfer across the cell wall, crossing of the plasma membrane and transfer inside the cell to the target, each step representing a potential barrier for the enzymatic inhibitor from being an effective antifungal drug, or a potential source of resistant strains against the drug.

The transferases which are responsible for creating the covalent bonds between the different polymers of the wall have been very little studied up till now.

These enzymes represent a better target than the chitin and glucan synthetase complexes since they are more easily accessible for a putative antifungal drug.

Nuoffer et al. (1991, Mol. Cell. Bio., 11, 27–37) have described a glycoprotein, named Gas1p, exposed on the surface of the yeast Saccharomyces cerevisiae. The genes coding for this protein have been cloned. The function of the Gas1p protein is not essential for the viability of the cell, and has not been determined.

Saporito-Irwing et al. (1995, Mol. Cell. Biol., 15, 601–613) have isolated a gene originating from the yeast Candida albicans, designated PHR1. The amino acid sequence determined for this protein PHR1 was 56% identical to that of the protein Gas1.

The gene was regulated in response to the pH of the culture medium. As for the protein gas1p, no function has been determined.

It clearly emerges from this analysis of the prior art that there has been a problem in obtaining molecules with effective antifungal activity.

The inventors have solved this problem.

They have shown that the introduction of mutations into a glucanosyltransferase originating from Aspergillus fumigatus interferes with the development of this microorganism.

They have also determined the sequences of several of these enzymes.

The present invention thus relates to a first protein with an activity of the β-(1-3)-glucanosyltransferase type characterized in that it has at least 50%, preferably 60%, and even more preferably 85% homology with proteins having the sequences, or a part of the sequences SEQ ID No 2 or SEQ ID No 3 as follows:

SEQ ID NO:2:

Met Lys Ala Ser Ala Val Thr Ala Ala Leu Ala Val Gly Ala
Ser Thr Val Leu Ala Ala Pro Ser Ile Lys Ala Arg Asp
Asp Val Thr Pro Ile Thr Val Lys Gly Asn Ala Phe Phe
Lys Gly Asp Glu Arg Phe Tyr Ile Arg Gly Val Asp Tyr
Gln Pro Gly Gly Ser Ser Asp Leu Ala Asp Pro Ile Ala
Asp Ala Asp Gly Cys Lys Arg Asp Ile Ala Lys Phe Lys
Glu Leu Gly Leu Asn Thr Ile Arg Val Tyr Ser Val Asp
Asn Ser Lys Asn His Asp Glu Cys Met Asn Thr Leu Ala
Asp Ala Gly Ile Tyr Leu Val Leu Asp Val Asn Thr Pro
Lys Tyr Ser Ile Asn Arg Ala Lys Pro Lys Glu Ser Tyr
Asn Asp Val Tyr Leu Gln Tyr Ile Phe Ala Thr Val Asp
Ala Phe Ala Gly Tyr Lys Asn Thr Leu Ala Phe Phe Ser
Gly Asn Glu Val Ile Asn Asp Gly Pro Ser Ser Ser Ala
Ala Pro Tyr Val Lys Ala Val Thr Arg Asp Leu Arg Gln
Tyr Ile Arg Ser Arg Lys Tyr Arg Glu Ile Pro Val Gly Tyr
Ser Ala Ala Asp Ile Asp Thr Asn Arg Leu Gln Met Ala
Gln Tyr Met Asn Cys Gly Ser Asp Asp Glu Arg Ser Asp
Phe Phe Ala Phe Ala Asn Asp Tyr Ser Trp Cys Asp Pro Ser
Ser Phe Lys Thr Ser Gly Trp Asp Gln Lys Val Lys Asn
Phe Thr Gly Tyr Gly Leu Pro Leu Phe Leu Ser Glu Tyr
Gly Cys Asn Thr Asn Lys Arg Gln Phe Gln Glu Val Ser
Ser Leu Tyr Ser Thr Asp Met Thr Gly Val Tyr Ser Gly
Gly Leu Val Tyr Glu Tyr Ser Gln Glu Ala Ser Asn Tyr
Gly Leu Val Glu Ile Ser Gly Asn Asn Val Lys Glu Leu
Pro Asp Phe Asp Ala Leu Lys Thr Ala Phe Glu Lys Thr
Ser Asn Pro Ser Gly Asp Gly Asn Tyr Asn Lys Thr Gly

Gly Ala Asn Pro Cys Pro Ala Lys Asp Ala Pro Asn Trp
Asp Val Asp Asn Asp Ala Leu Pro Ala Ile Pro Glu Pro
Ala Lys Lys Tyr Met Thr Glu Gly Ala Gly Lys Gly Pro
Gly Phe Ala Gly Pro Gly Ser Gln Asp Arg Gly Thr Gln
Ser Thr Ala Thr Ala Glu Pro Gly Ser Gly Ser Ala Thr
Gly Ser Ser Ser Ser Gly Thr Ser Thr Ser Ser Lys Gly
Ala Ala Ala Gly Leu Thr Val Pro Ser Leu Thr Met Ala
Pro Val Val Val Gly Ala Val Thr Leu Leu Ser Thr Val
Phe Gly Ala Gly Leu Val Leu Leu

SEQ ID NO: 3: (BGT2)
Asp Asp Val Thr Pro Ile Thr Val Lys Gly Asn Ala Phe Phe
Lys Gly Asp Glu Arg Phe Tyr Ile Arg Gly Val Asp Tyr
Gln Pro Gly Gly Ser Ser Asp Leu Ala Asp Pro Ile Ala
Asp Ala Asp Gly Cys Lys Arg Asp Ile Ala Lys Phe Lys
Glu Leu Gly Leu Asn Thr Ile Arg Val Tyr Ser Val Asp
Asn Ser Lys Asn His Asp Glu Cys Met Asn Thr Leu Ala
Asp Ala Gly Ile Tyr Leu Val Leu Asp Val Asn Thr Pro
Lys Tyr Ser Ile Asn Arg Ala Lys Pro Lys Glu Ser Tyr
Asn Asp Val Tyr Leu Gln Tyr Ile Phe Ala Thr Val Asp
Ala Phe Ala Gly Tyr Lys Asn Thr Leu Ala Phe Phe Ser
Gly Asn Glu Val Ile Asn Asp Gly Pro Ser Ser Ser Ala
Ala Pro Tyr Val Lys Ala Val Thr Arg Asp Leu Arg Gln
Tyr Ile Arg Ser Arg Lys Tyr Arg Glu Ile Pro Val Gly Tyr
Ser Ala Ala Asp Ile Asp Thr Asn Arg Leu Gin Met Ala
Gln Tyr Met Asn Cys Gly Ser Asp Asp Glu Arg Ser Asp
Phe Phe Ala Phe Asn Asp Tyr Ser Trp Cys Asp Pro Ser
Ser Phe Lys Thr Ser Gly Trp Asp Gln Lys Val Lys Asn
Phe Thr Gly Tyr Gly Leu Pro Leu Phe Leu Ser Glu Tyr
Gly Cys Asn Thr Asn Lys Arg Gln Phe Gin Glu Val Ser
Ser Leu Tyr Ser Thr Asp Met Thr Gly Val Tyr Ser Gly
Gly Leu Val Tyr Glu Tyr Ser Gln Glu Ala Ser Asn Tyr
Gly Leu Val Glu Ile Ser Gly Asn Asn Val Lys Glu Leu
Pro Asp Phe Asp Ala Leu Lys Thr Ala Phe Glu Lys Thr
Ser Asn Pro Ser Gly Asp Gly Asn Tyr Asn Lys Thr Gly
Gly Ala Asn Pro Cys Pro Ala Lys Asp Ala Pro Asn Trp
Asp Val Asp Asn Asp Ala Leu Pro Ala Ile Pro Glu Pro
Ala Lys Lys Tyr Met Thr Glu Gly Ala Gly Lys Gly Pro
Gly Phe Ala Gly Pro Gly Ser Gln Asp Arg Gly Thr Gln
Ser Thr Ala Thr Ala Glu Pro Gly Ser Gly Ser Ala Thr
Gly Ser Ser Ser Ser Gly Thr Ser Thr Ser Ser Lys Gly
Ala Ala Ala Gly Leu Thr Val Pro Ser Leu Thr Met Ala
Pro Val Val Val Gly Ala Val Thr Leu Leu Ser Thr Val
Phe Gly Ala Gly Leu Val Leu Leu

This protein preferably has a molecular weight of about 44 kD, or of about 49 kD if it carries at least one residue of the N-glycosyl type.

The present invention also relates to proteins with β-(1-3)-glucanosyltransferase activity characterized in that they have at least 50%, preferably 60% and even more preferably 85% homology with proteins having the sequences, or a part of the sequences SEQ ID No 10 or SEQ ID No 12 as follows:

SEQ ID No 10:
Gly Phe Phe Ala Gly Asn Glu Val Ile Asn Glu Gln Ser Val
Lys Asn Val Pro Thr Tyr Val Arg Val Cys His Pro Ser
Pro Gln Leu Thr Ile Ala Cys Pro Leu

SEQ ID No 12 (BGT4)
Gly Phe Phe Ala Gly Asn Glu Val Val Asn Gln Ala Asn
Gln Ser Ala Gly Ala Ala Phe Val Lys Ala Ala Ala Arg
Asp Met Lys Ala Tyr Ile Lys Thr Lys Lys Gly Tyr Arg Gln
Ser Leu Ala Ile Gly Tyr Ala Thr Thr Asp Asn Pro Glu
Ile Arg Leu Pro Leu Ser Asp Tyr Leu Asn Cys Gly Asp
Gln Ala Asp Ala Val Asp Phe Phe Gly Tyr Asn Ile Tyr
Glu Trp Cys Gly Asp Gln Thr Phe Gln Thr Ser Gly Tyr
Gln Asn Arg Thr Glu Glu Tyr Lys Asp Tyr Ser Ile Pro
Ile Phe Ile Ser Glu Tyr Gly Cys Asn

The present invention also relates to fragments of these proteins.

Said invention is not limited to the proteins having the sequences SEQ ID No 2, SEQ ID No 3, SEQ ID No 10 or SEQ ID No 12 but extends to any protein having sequences similar to those having the sequences SEQ ID No 2, SEQ ID No 3, SEQ ID No 10 or SEQ ID No 12 and in particular having certain amino acid substitutions in which an amino acid is replaced by another amino acid having essentially the same physico-chemical properties. Lehninger's biochemistry manual (Flammarion Medecine-Science, 1977, or one of its more recent editions) distinguishes four groups of amino acids, based on their physico-chemical behavior: those with a non-polar or hydrophobic side-chain, those with an uncharged polar side-chain, those with a negatively charged side-chain, and those with a positively charged side-chain.

The present invention also relates to nucleotide sequences coding for proteins, or protein fragments such as those described above, and more particularly DNA sequences (cDNA or genomic DNA) or RNA sequences.

Such a DNA sequence may be that having at least 50%, preferably 60% and even more preferably 85% homology with the genomic sequence SEQ ID No 1, or a part of the sequence SEQ ID No 1 as follows:

ATG AAG GCC TCT GCT GTT ACT GCC GCT CTC
GCC GTC GGT GCT TCC ACC GTT CTG GCA GCC
CCC TCC ATC AAG GCT CGT GAC GAC GTT ACT
CCC ATC ACT GTC AAG GGC AAT GCC TTC TTC
AAG GGC GAT GAG CGT TTC TAT ATT CGC GGT
GTC GAC TAC CAG CCC GGT GGC TCC TCC
GAC CTG GCT GAT CCC ATC GCT GAT GCC GAT
GGT TGC AAG CGT GAC ATT GCC AAG TTC AAG
GAG CTG GGC CTG AAC ACT ATC CGT GTC TAC
TCG GTC GAC AAC TCC AAG AAC CAC GAT
GAG TGT ATG AAT ACA CTG GCT GAT GCT GGC
ATC TAT CTG GTG CTC GAT GTC AAC ACT CCC
AAG TAC TCC ATC AAC CGC GCC AAG CCT AAG
GAG TCG TAC AAC GAT GTC TAC CTC CAG TAT
ATC TTC GCT ACC GTT GAT GCT TTC GCC GGT
TAC AAG AAC ACC CTC GCT TTC TTC TCC GGC
AAC GAG GTT ATC AAC GAT GGC CCT TCC TCC
TCT GCT GCT CCC TAC GTC AAG GCC GTC ACT
CGT GAT CTG CGT CAG TAC ATC CGT AGC CGC
AAG TAC CGT GAG ATT CCT GTC GGC TAC TCG
GCT GCC GAT ATC GAC ACC AAC CGT CTT CAG
ATG GCC CAG TAT ATG AAC TGC GGT TCC GAC
GAC GAG CGC AGT GAC TTC TTC GCT TTC AAC
GAC TAC TCC TGG TGC GAT CCC TCC TCT TTC
AAA ACC TCG GGC TGG GAT CAG AAG GTC
AAG AAC TTC ACT GGC TAC GGT CTT CCT CTC
TTC CTG TCC GAA TAC GGC TGC AAC ACC AAC
AAG CGT CAA TTC CAA GAA GTC AGC TCT CTC
TAC TCC ACG GAC ATG ACT GGT GTC TAC TCT
GGT GGT CTC GTG TAC GAG TAC TCT CAG GAG
GCC AGC AAC TAC GGT CTG GTG GAG ATT AGC
GGC AAC AAT GTC AAG GAG CTC CCA GAC
TTC GAC GCT CTG AAG ACC GCG TTC GAA
AAG ACC TCC AAC CCC TCC GGC GAC GGC
AAC TAC AAC AAG ACT GGT GGT GCC AAC
CCT TGC CCC GCT AAG GAC GCT CCC AAC TGG
GAC GTT GAC AAC GAT GCT CTT CCT GCC ATC
CCC GAG CCC GCC AAG AAG TAC ATG ACT
GAG GGT GCT GGC AAG GGC CCT GGT TTT
GCC GGA CCT GGC AGC CAG GAC CGT GGT
ACC CAG TCC ACT GCC ACT GCT GAG CCC
GGA TCT GGC TCT GCC ACT GGA AGC AGC AGC
AGC GGC ACC TCC ACC TCT TCC AAG GGC GCT
GCA GCT GGC CTG ACT GTC CCT AGC CTG ACC
ATG GCT CCC GTT GTC GTT GGT GCG GTT ACA

CTC CTG TCC ACC GTC TTC GGC GCT GGC CTC
GTC CTC TTG T GA

This sequence has been included in a 2.2 kb fragment, which has itself been included in the X bal site of the pUC19 vector (Maniatis et al., 1989, Cold Spring Harbor Laboratories Press). The strain *E. coli* DH$_5$α carrying this modified vector was deposited in the Collection Nationale de Culture de Micro-Organismes at the Institut Pasteur (CNCM) on the Jul. 26, 1996 under the number I-1763.

Such a sequence may also be that having at least 50%, preferably 60% and even more preferably 85% homology with the complementary DNA sequence comprised in a 1.4 kb fragment, which has been included in the pCRII vector (In Vitrogen). This, carried by the *E. coli* DH$_5$α strain, was deposited in the Collection Nationale de Culture de Micro-Organismes at the Institut Pasteur (CNCM) on the Jul. 26, 1996 under the number I-1762.

These two strains are objects of the present invention.

Nucleotide sequences according to the present invention may also be those having at least 50%, preferably 60%, and even more preferably 85% homology with one of the DNA sequences SEQ ID No 9 or SEQ ID No 11 as follows:

SEQ ID No 9:
GGCTTCTTCG CCGGCAACGA GGTTATCAAC
GAGCAGAGTG TCAAGAACGT TCCCACTFAC
GTCCGGGTAT GTCATCCATC CCCACAGCTT
ACGATTGCCT GTCCACTGAC ACTCTCGTAG
GCGACTCAGC GTGACATGAA GGACTACTAC
GCAAAGAACC TTGACCGCAG CATTCCTGTT
GGCTATTCTG CTGCCGATAT TCGTCCCATC
CTCATGGCAC CCCTCAACTA CTTCATGTGC
GCTGACGATG CTAATTCCCA ATCGGACTTC
TTCGGCCTCA ACTCCTACTC GTGGTGCGGC
AACTCGTCCT ACACCAAGAG TGGCTACGAT
GTCCTCACCA AGGACTTTGC CGACGCCTCT
ATCCCCGTCT TCATCTCCGA ATTCGGCTGC
AACA

SEQ ID No 11
GGTTTCTTCG CCGGCAACGA GGTTGTGAAT
CAGGCGAATC AGTCCGCCGG CGCTGCATTC
GTCAAGGCCG CCGCGCGAGA CATGAAGGCC
TACATCAAGA CCAAGGGATA CCGGCAATCG
CTGGCAATTG GATACGCGAC CACTGACAAC
CCGGAAATCC GACTCCCGCT GTCCGACTAC
CTCAACTGCG GCGACCAGGC CGACGCGGTC
GACTTCTTCG GCTACAACAT CTACGAATGG
TGCGGTGACA AGACCTTCCA GACCTCGGGC
TACCAGAACC GCACCGAGGA GTACAAGGAC
TACTCCATCC CCATCTTCAT CTCCGAATAC
GGCTGCAAC

These two sequences have been independently included in the pCRII vectors and introduced into the *E. coli* DH$_5$α strain. These strains were deposited in the Collection Nationale de Culture de Micro-Organismes at the Institut Pasteur (CNCM) on the Aug. 22, 1997 under the numbers I-1914 and I-1913.

A further object of the present invention is a method for the detection of proteins with a strong homology with the sequence of the protein BGT2.

The present invention thus relates to a method for detecting a nucleotide sequence having at least 60% identity with the sequence SEQ ID No 1 in a biological sample containing nucleotide sequences, comprising the following steps:

a) placing the biological sample in contact with the nucleotide primers P3 and P4 having the sequences SEQ ID No 7 and SEQ ID No 8, respectively, as follows:

SEQ ID No 7:
GSYTTCTTCK CYGGCAACGA GGTT
SEQ ID No 8:
GTTGCAGCCG WATTCGGASA YGAA the nucleotide sequences contained in the sample having been if necessary put into a form enabling their hybridization under conditions enabling the hybridization of the primers with the nucleotide sequences.

b) amplification of the nucleotide sequences
c) revealing the amplification products, and
d) detection of the mutations by appropriate methods.

The proteins according to the invention may be obtained by purification of an autolysate of *Aspergillus fumigatus*. The protein may be purified by four steps of ion-exchange chromatography and one step of gel filtration.

Said proteins may also be obtained by genetic engineering methods. For example, the sequence SEQ ID No 1, if possible without its C-terminal part, may be cloned in an appropriate vector, and expressed in an expression system, such as the *Pichia pastoris* system, marketed by In Vitrogen.

In this system, the sequence of the gene coding for the protein is cloned in an expression vector, then linearized. Protoplasts originating from *P. pastoris* are transformed with the linearized vector.

The clones, in which a recombination is performed and which replaces the aoxl sequence by the sequence of the gene of the protein which it is desired to produce, are selected for their capacity to grow in a histidine-deficient medium. A person skilled in the art may refer to "Manual of methods for expression of recombinant proteins in *Pichia pastoris*", published by In Vitrogen.

The protein thus expressed, if possible secreted in the culture medium, is recovered by processes known to a person skilled in the art.

Such a protein may be used, in particular, for screening molecules to identify their antifungal activity.

Thus, another object of the present invention is a process for screening molecules to identify their antifungal activity comprising the following steps:

placing together the molecules to be screened and the protein or the protein fragment as described above, or coded by a sequence such as described above, and determining the effect of the molecule on said protein.

The determination of the effect of the molecules on said protein may be accomplished by measuring the activity of the β-(1-3) glucanosyltransferase (BGT2). Such activity may be determined by placing said protein in the presence of a substrate on which it has an effect, which may be composed of laminarioligosaccharides comprising at least 10 glucosyl radicals linked by β-(1-3) bonds. When the protein is active, it cleaves a part of the molecule and binds the fragment obtained onto the non-reducing terminal of an uncleaved substrate molecule.

The product resulting from the activity of the protein is in the form of coupling products of two laminarioligosaccharides. This product may be detected by any process allowing the separation of oligosaccharides with different degrees of polymerization, in particular by chromatographic methods, such as high-pressure liquid chromatography (HPLC) or thin-layer chromatography (TLC). This latter method, although less precise than the first, is the easier to use.

For the use of these chromatographic methods, a person skilled in the art may consult the following manual: Carbohydrate analysis : a practical approach. Chaplin and Kennedy, 1986 IRC Press, Oxford.

This detection method enables determination as to whether the molecules detected have antifungal activity.

These molecules having antifungal activity show effects on the β-(1-3)glucanosyltransferase activity of said proteins. These effects may be for example the inhibition of this activity.

The present invention also relates to molecules having an effect on said proteins, which may be detected by the process as described above, as well as the use of these molecules to prepare a drug, or for the treatment of diseases related to fungi, in vertebrates and plants.

One of the advantages of the use of these molecules lies in the low frequency of appearance of resistant strains of the fungi, in contrast to other known antifungal molecules.

The present invention is illustrated, without being limited, by the following examples:

FIG. 1 illustrates an analysis of the SDS-PAGE type of the purified 49 kDa protein: line a, molecular weight standards; line b, purified 49 kDa protein (1.5 μg); line c, purified 49 kDa protein (1.5 μg) after treatment with N-glycosidase F; line d, N-glycosidase alone. The molecular weights of the protein bands and N-glycosidase F are shown.

FIG. 2 represents an HPAEC-type analysis of the products arising from the incubation of the 49 kDa enzyme with the reduced laminarioligosaccharides. The purified 49 kDa protein was incubated with 8 mM of reduced laminarioligosaccharides of size $G_{11}$, $G_{12}$, $G_{13}$ or $G_{14}$ (reduced laminarioligosaccharides with 11, 12, 13 or 14 glucose residues respectively) and the HPAEC profiles arising from these samples are shown at time zero and 15 min with the sizes of the main products.

FIG. 3 represents an HPAEC-type analysis of the products arising from the incubation of the 49 kDa enzyme with 8 mM of $rG_{16}$. The HPAEC profiles arising from these samples are shown at time zero, 30 min and 120 min, with the sizes of the main products.

FIG. 4 illustrates the action of the transferase and the products formed from the reduced laminarioligosaccharides.

FIG. 5 shows the effect of varying concentrations of the substrates. The 49 kDa transferase was incubated with 3 μM of [$^3$H]-$rG_{11}$ (1×10$^6$ cpm) plus varying quantities of unmarked $rG_{11}$. The % of transfer was determined by comparing the proportion of marking formed in the form of $rG_6$ and $rG_{16}$. The inset shows the same data with the concentration of the substrates presented in the form of a linear scale.

FIG. 6 illustrates the effect of pH on the transfer rate. The 49 kDa transferase was incubated with 8 μM of [$^3$H]-$rG_{11}$ (1×10$^6$ cpm). The reaction rates were determined by measuring the quantity of marking formed in the form of the product $rG_{16}$. The buffers used were: ●, sodium citrate/citric acid; o, imidazole/citric acid; x, sodium acetate/acetic acid; ■, Tris/glycine; ▼, phosphate/NaOH; □, Tris/acetic acid; Δ, glycine/HCl.

FIG. 7 shows the sequence originating from the gene BGT2 from *A. fumigatus* (A) compared with genes PHR1 and GAS1 isolated from *C. albicans* (C) and *S. cerevisiae* (S). The underlined amino acid sequence corresponds to the presumed intron.

FIG. 10 is a comparison of the sequences of the protein with sequence SEQ ID No 2 and the five following proteins: Phr 1p, Gas 2p, Gas 3p, Gas 4p and Gas 5p.

EXAMPLES

Experimental Procedures

Figure 1:
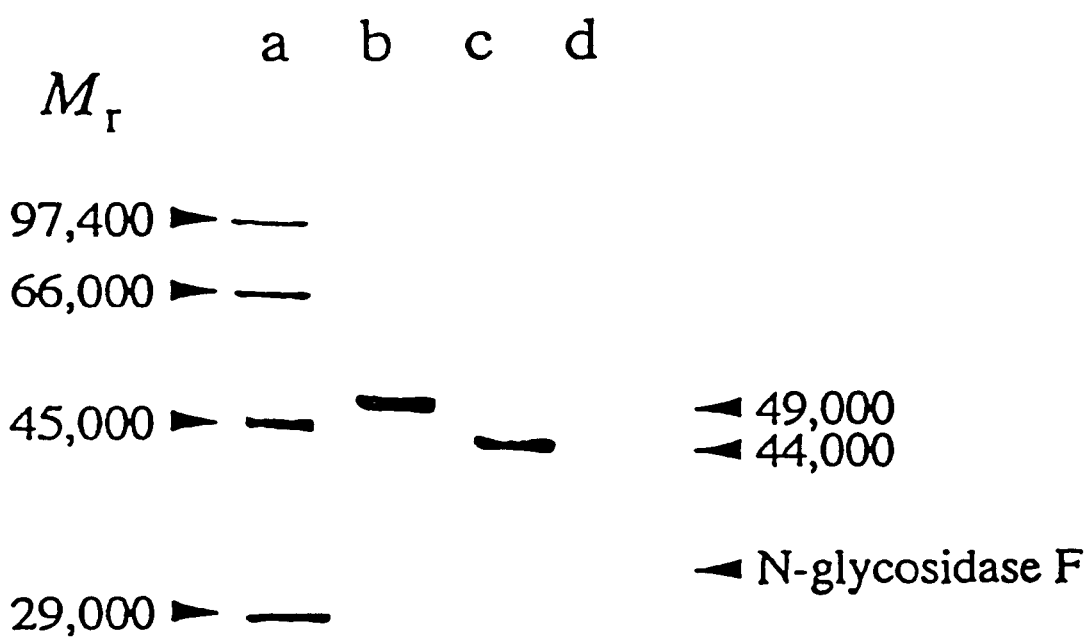

1. Preparation of the Cell Wall and Autolysis.

The strain CBS 144-89 of type *A. fumigatus* (available from the Collection Centralbureau voor Schimmelculture) was grown in a 15 L fermenter in 2% glucose, 1% mycopeptone (Biokar Diagnostics) plus 0.1% silicone antifungal 426R (Rhodorsil) at 25° C. (agitation at 500 r.p.m., aeration 0.5 vol.vol$^{-1}$. min$^{-1}$. for 42 h). A culture which had grown for 3 days in a 2L fermenter under the same conditions was used as the inoculum (8%(v/v)). The mycelia were collected by filtration under vacuum and ruptured by passing through a Dyno type mixer in the presence of glass beads (W. A. Bachofen AG, Basel, Switzerland) (0.5–0.75 mm diameter). The progression of the disruption of the cells was monitored microscopically. The suspension of the ruptured mycelia was centrifuged (8000 g, 15 min) and the residue containing the cell walls was washed 3 times with water and once with 50 mM Na acetate, pH 5.6 containing 5 mM Na azide, then resuspended in the same buffer (250 g wet weight per L of buffer) and incubated (agitation 200 r.p.m.) at 37° C. After 72 h, the suspension was centrifuged (10000 g, 15 min) and the supernatant was placed in a dialysis tube, concentrated 5 to 10 times with polyethylene glycol 20000, dialyzed against 5 mM Na acetate, pH 5.6, recentrifuged (10000 g, 15 min) and filtered (0.45 μm filter). This preparation is subsequently referred to as the autolysate.

2. Enzyme Purification

The fractions collected during each step of the chromatography were tested for enzymatic activity using the non-radioactive transferase test (see below). The dialyzed and concentrated autolysate was applied to a 4×18 cm DEAE-SEPHAROSE FAST-FLOW column (Pharmacia) equilibrated with 5 mM Na acetate, pH 5.6, and the column was eluted with a linear gradient up to 1M NaCl (2000 ml) at a flow rate of 240 ml.hr$^{-1}$. The fractions containing transferase activity were collected, dialyzed against a buffer containing 10 mM β-mercaptoethanol, 5 mM EDTA, 10 mM Na acetate, pH 4.0, applied to a MONO S column (HR 5/5 Pharmacia), and eluted with a linear gradient of NaCl (0 to 300 mM in 40 min) at a flow rate of 0.8 ml.min$^{-1}$. The fraction containing transferase was collected, dialyzed against 10 mM Tris/HCl, pH 7.0, and applied to a DEAE-5PW column (8×75 mm, TosoHaas), and eluted with a linear gradient up to NaCl (0 to 300 mM in 60 min) with a flow rate of 0.75 ml.min$^{-1}$. The fractions containing transferase activity were collected, dialyzed against a buffer containing 10 mM β-mercaptoethanol, 5 mM EDTA 10 mM EDTA, 10 mM Na acetate, pH 4.0, and applied to a CM-5PW column (8×75 mm, TosoHaas), and eluted with a linear gradient of NaCl (0 to 300 mM in 60 min) with a flow rate of 0.8 ml.min$^{-1}$. The fractions containing transferase activity were collected and concentrated by a speed-vac and fractionated on a SUPERDEX HR75 column (Pharmacia) equilibrated with 10 mM Tri/HCl, pH 7.0 containing 150 mM NaCl, at a flow rate of 0.75 ml.min$^{-1}$. The fractions containing purified transferase were collected, dialyzed against 5 mM Na citrate, pH 5.0, concentrated by speed-vac and stored at −20° C. until used.

3. Transferase Assays

The enzyme fractions were assayed for transferase activity by incubation in 50 mM Na citrate, pH 5.0 at 37° C. (10 μl volume per assay) with a laminarioligosaccharides reduced with borohydride (8 mM final) of at least size $G_{10}$. Samples (3 µl) were taken at different times, 50 mM NaOH cooled in ice (47 µl) was added to terminate the reaction, and the mixture was frozen until analyzed by high-performance anion-exchange chromatography (HPAEC). Since the peak intensities detected by Pulsed Electrochemical Detector (PED) varied from day to day, the transferase activity was quantified by use of reduced laminarioligosaccharides marked with $^3H$ as substrates and measurement of the appearance of the marking in the products after separation by HPAEC chromatography, using the on-line Radiomatic 150TR scintillation rate analysis apparatus (Packard).

Except where otherwise mentioned, the assays for the enzyme characterization studies were performed as above with 0.25 µg of purified transferase.

4. Colorimetric Determinations

The β-glucanase activity was measured in the protein fractions by a sugar reduction test using the reagent hydroxybenzoic acid hydrazide with laminarin reduced by borohydride instead of carboxymethyl pachyman as substrate (Ram et al., 1988, Life Sci Adv., 7, 379–383). The exo-β-glucanase/β-glucosidase activities were measured by incubating the enzyme fractions with p-nitrophenyl-β-D-glucopyranoside (Hartland et al., 1991, Proc. R. Soc. London B, 246, 155–160). The quantity of the proteins was estimated using the Biorad protein test according to the manufacturer's instructions, with bovine serum albumin as standard.

5. High-performance Anion-exchange Chromatography

The samples from the transferase tests were analyzed on a Dionex CARBOPAC PA1 analytical column (4×250 mm) (with a Pa1 reference column) on a Dionex HPAEC-type system with pulsed electrochemical detection (PED-2 cell), fitted with a combination of pH-Ag/AgCl reference electrodes and using a potential of 0.4 V for the first 0.5 s of detection. The oligosaccharides were eluted under the following conditions: flow rate 1 ml/min, buffer A: 50 mM NaOH; buffer B: 500 mM sodium acetate in 50 mM NaOH; gradient 0 to 2 min, 98% A 2% B (isocratic), 2 to 15 min 75% A 25% B (linear 15 to 45 min 60% A 40% B (linear).

The laminarioligosaccharide standards were obtained from Seikagaku (Japan).

6. Thin-layer Chromatography (TLC)

The laminarioligosaccharides were revealed by thin-layer chromatography on silica gel 60 (Kieselgel, Merck) using n-butanol/acetic acid/water (2/1/1.5) as eluant and sulfuric orcinol coloration.

The degree of polymerization (dp) of the oligosaccharides was also determined by HPAE-type chromatography using a pulsed electrochemical detector and an anion-exchange column (CARBO6PAC PA1, 4.6×250 mm, Dionex).

7. Preparation of Reduced Substrates

The laminarioligosaccharides were obtained by partial acid hydrolysis (6.5 M TFA, 15 min, 100° C., followed by 1 M TFA, 45 min, 100° C.) of curdlan (Serva). The TFA was removed by rotary evaporation in the presence of methanol. The oligosaccharides were reduced overnight with $NaBH_4$ (1:0.5 (w/w)) in 0.1 M NaOH at room temperature). The reduced ends of the laminarioligosaccharides marked with $^3H$ were similarly prepared by reduction with $NaB^3H_4$ (Amersham, 20–40 Ci/mmol, 10 mCi per mg of oligosaccharide) overnight followed by a subsequent reduction by $NaBH_4$ as before.

The excess of $NaBH_4$ was destroyed by addition of acetic acid up to pH 5–6, and the borate salts were removed by rotary evaporation in the presence of methanol. The reduced oligosaccharides were desalted by gel filtration on a SEPHADEX G15 column (1.2×80 cm, 8 ml.h$^{-1}$, equilibrated in water) and collected after detection by the orcinol-sulfuric acid method (Ashwell, 1966, Methods Enzymol, 8, 85–95). The laminarioligosaccharides were separated by HPAEC on a CARBOPAC PA1 preparative column (9×250 mm, Dionex) with a Na acetate gradient 15 to 350 mM in 50 mM NaOH, (45 min) at a flow rate of 4 ml.min$^{-1}$. The oligosaccharide fractions collected were neutralized with acetic acid, desalted by gel filtration on a SEPHADEX G15 column as described above, then lyophilized. The laminarin (Sigma) was reduced in the same way, but desalted by dialysis against 0.5% acetic acid, followed by dialysis against water, then lyophilized. The gentiooligosaccharides were prepared as above (without reduction) from pulsatin (Calbiochem) which had been finely divided with a pestle and mortar. The maltoheptaose and cellopentaose were from Boehringer Mannheim and Sigma, respectively. The chitohexaose was a gift from Dr. A Domard (Université Claude Bernard, Villeurbanne, France). $G_{10}$ reduce with borohydride containing a β-(1-6) intrachain bond at the sixth link from the reduced end ($rG_{10}$*) was obtained by incubating the reduced laminarihexose ($rG_6$) with an enzyme homologous with the BGT1 enzyme from Candida purified from A. fumigatus. The product from the transferase $rG_{10}$* was separated and purified as for the laminarioligosaccharides.

7. Electrophoresis on SDS-polyacrylamide Gel

The protein samples were analyzed by SDS-PAGE (Laemmli, 1970, Nature, 227, 680–685) using 10% separation gels and 4% stacked gels. The protein bands were revealed by coloration with Coomassie blue. The N-glycosylation of the glycoproteins was performed using the recombinant N-glucosidase F (Oxford GlycoSystems) according to the manufacturer's instructions.

8. $^1H$ NMR Spectroscopy

Two samples were analyzed: the reduced laminarioligosaccharide $G_{10}$ used as standard and a reduced oligosaccharide $G_{16}$ obtained after incubation of $rG_{10}$ with the transferase and purified by HPAEC. The deuterium in the samples dried by lyophilization was replaced by dissolution in $D_2O$ (99.95%, Solvents Documentation Synthese, France). The spectra were recorded at 300 K and 318 K on Variant Unity 500 spectrometer operating at a proton frequency of 500 MHz. The OH resonance of the residual water was removed by selective radiation during the relaxation time. Sodium 3-trimethylsilylpropionic acid was used as external standard.

Example 1

Purification of the 49 kDa Protein

A high-performance anion-exchange chromatography (HPAEC) test using laminarioligosaccharides reduced with borohydride as substrates was developed to study the activities of the β-glucanosyl transferase associated with the cell wall of A. fumigatus. A new β-(1-3)-glucosyl transferase activity was detected in the semi-purified fractions from the autolysate of the cell wall of A. fumigatus, which remained associated with a 49 kDa protein throughout its purification.

The protein was purified to apparent homogeneity with four steps of ion-exchange chromatography and one gel filtration step.

The activity of the transferase was clearly detectable after only the second chromatography step (MONO S). The analysis by SDS-PAGE of the purified fraction showed a main band at 49 kDa (FIG. 1, well b). In order to determine if it contained an N-linked carbohydrate, the protein was digested with N-glucosidase F. The digested protein passed on SDS-PAGE as 44kDa protein, (FIG. 1, well c) showing that it contained about 5 kDa of N-linked carbohydrate.

Example 2

Enzymatic Activity of the 49 kDa Protein

HPAEC analysis of the products resulting from the incubation of the 49 kDa protein with a laminarioligosaccharide reduced with borohydride ($rG_n$) of size $G_{10}$ or larger led to the characterization of a new activity of glucanosyl transferase type.

Figure 2:
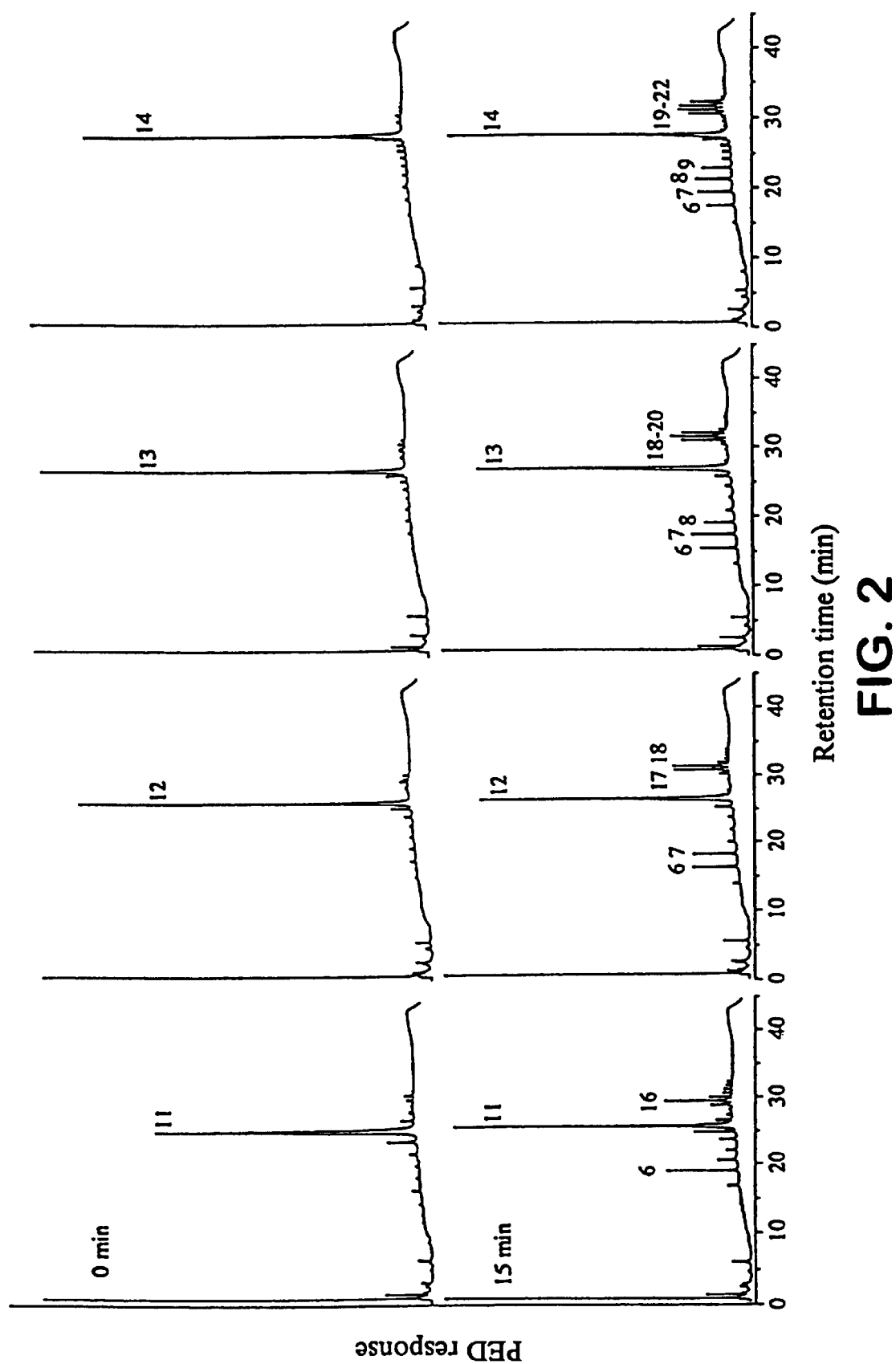

The principal initial products arising from the incubation with $rG_{11}$ were $rG_6$ and $rG_{16}$; $rG_{12}$ gave $rG_6$+$rG_7$ and $rG_{17}$+$rG_{18}$, $rG_{13}$ gave $rG_6$ to $rG_8$ and $rG_{18}$ to $rG_{20}$, and $rG_{14}$ gave $rG_6$ to $rG_9$ and $rG_{19}$ to $rG_{22}$ (FIG. 2). Significantly, no products of the laminarioligosaccharide type, reduced or not, were detected, confirming the absence of any endo-β-(1-3)-glucanase activity. The presence of such activity would have caused the formation of a mixture of hydrolysis products, reduced or not, the latter having different retention times. In addition, no glucose was detected, and together with the absence of hydrolysis of p-nitrophenyl-β-glucopyranoside and the formation in the network of reducing sugar arising from the laminarin reduced with borohydride in the corresponding colorimetric tests, this confirmed the absence of exo-β-(1-3)-glucanase and β-glucosidase activity.

The profile of the products obtained (FIG. 2) is in agreement with an endogenous type of glucanosyl transferase activity in which the glucan chain is cleaved by an endolytic cleavage, freeing the portion of the reduced end, and the remainder is transferred to another glucan chain, to form a larger transferase product. Thus, in the simplest reaction with $rG_{11}$, the enzyme cleaves the substrate, liberating $rG_6$ from the reduced end of the substrate molecule, and the remaining $G_5$ is then transferred to another $rG_{11}$ molecule acting as receptor, to form a transferase-type product $rG_{16}$:

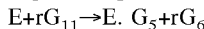
E+$rG_{11}$→E. $G_5$+$rG_6$
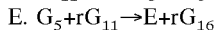
E. $G_5$+$rG_{11}$→E+$rG_{16}$ where E represents the enzyme. The transferase cleaves $rG_{12}$ in two different places, leading to two different transferase-type products:

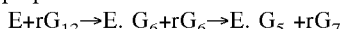
E+$rG_{12}$→E. $G_6$+$rG_6$→E. $G_5$ +$rG_7$
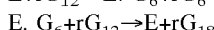
E. $G_6$+$rG_{12}$→E+$rG_{18}$
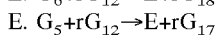
E. $G_5$+$rG_{12}$→E+$rG_{17}$ Similarly with $rG_{13}$ and $rG_{14}$, the transferase cleaves in three or four different places, respectively, each time transferring the part of the non-reduced end to another acceptor molecule $rG_{13}$ or $rG_{14}$.

Additional analyses of incubations of the 49 kDa transferase with reduced or smaller laminarioligosaccharides showed that the reaction with $rG_{10}$ gave $rG_5$+$rG_6$ and $rG_{14}$+$rG_{15}$, as initial major products, while the reaction with $rG_9$ was extremely slow, forming small peaks of $rG_5$ to $rG_9$ and $rG_{10}$ to $rG_{13}$. No products were detected after incubation with laminarioligosaccharides of size $G_8$ or smaller.

In order to determine the relative reaction rate of the enzymes with laminarioligosaccharides of variable sizes, the 49 kDa enzyme (0.25 μg) was incubated with 8 mM of $rG_{10}$ to $rG_{15}$ marked with ³H and the rate of formation of the marked products was measured. The rate with $rG_{10}$ (328 nmol.min⁻¹) was approximately equal to 50% of that with the larger substrates and there was no significant difference between the reaction rates for $rG_{11}$ to $rG_{15}$ (648±46 nmol.min⁻¹.mg proteins⁻¹).

Figure 3:
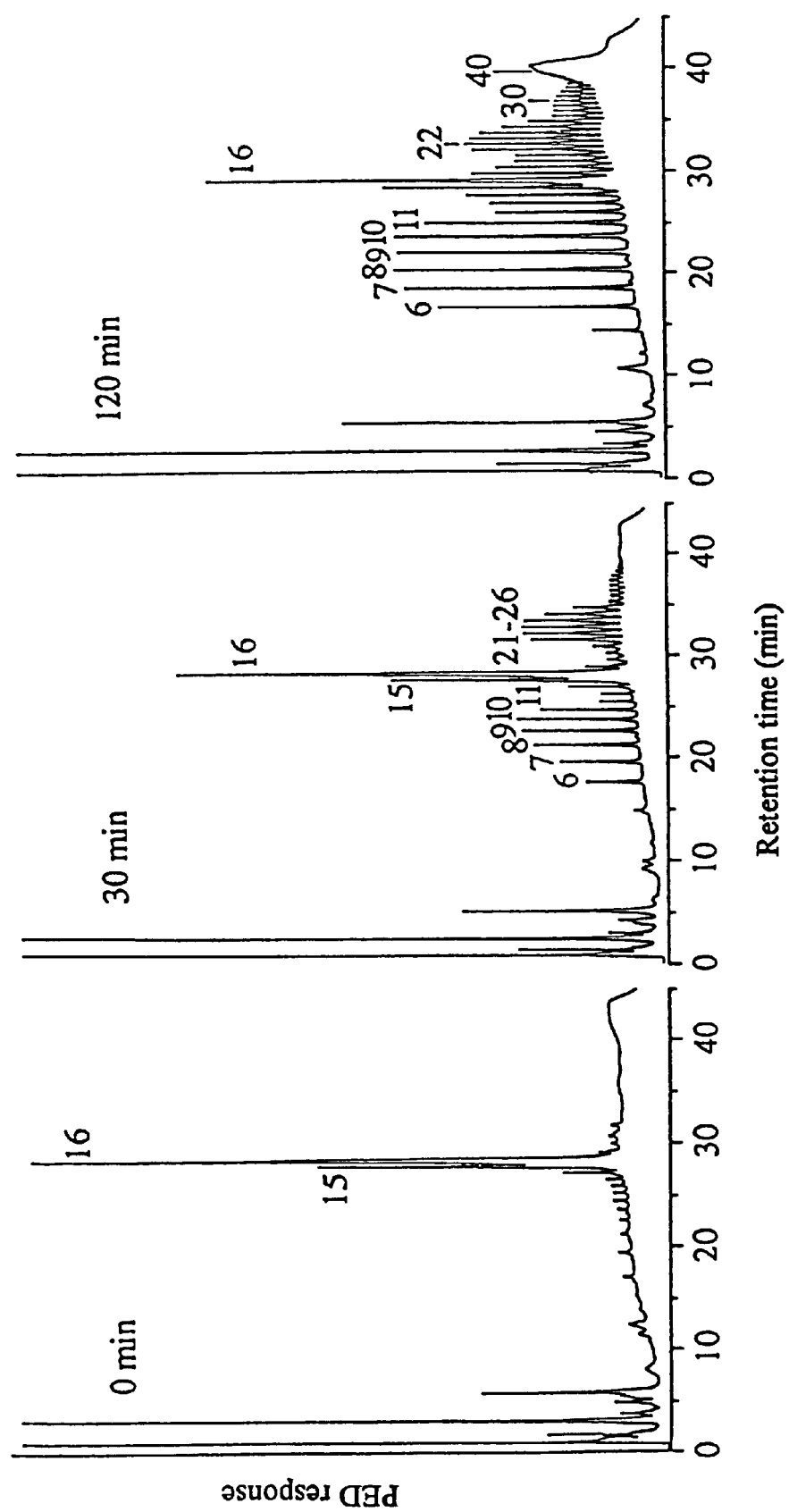

Analysis of longer incubations of the purified enzymes with reduced laminarioligosaccharides of size at least $G_{10}$ showed that the products from the initial transferase could be re-used either as donors or as acceptors, leading to the formation of products of increasing size, until they are eliminated from the solution because of their insolubility in the aqueous buffer. An incubation of 30 min with $rG_{16}$ (containing some contaminating $rG_{15}$) led to the formation of reduced initial major products of sizes $G_6$ to $G_{11}$ and $G_{21}$, to $G_{26}$ (FIG. 3), but after 120 mm, larger transferase products appeared with sizes of at least $G_{40}$ (FIG. 3). The products with sizes $G_{29}$ and larger precipitated at the bottom of the incubation tube since they were absent when the reaction mixture was briefly centrifuged and the supernatant analyzed. Incubation of the purified enzyme with reduced laminarin led to the production of smaller and larger products, showing that soluble oligosaccharides of size at least $G_{30}$ and larger can act as donors and acceptors in the reaction.

Figure 4:
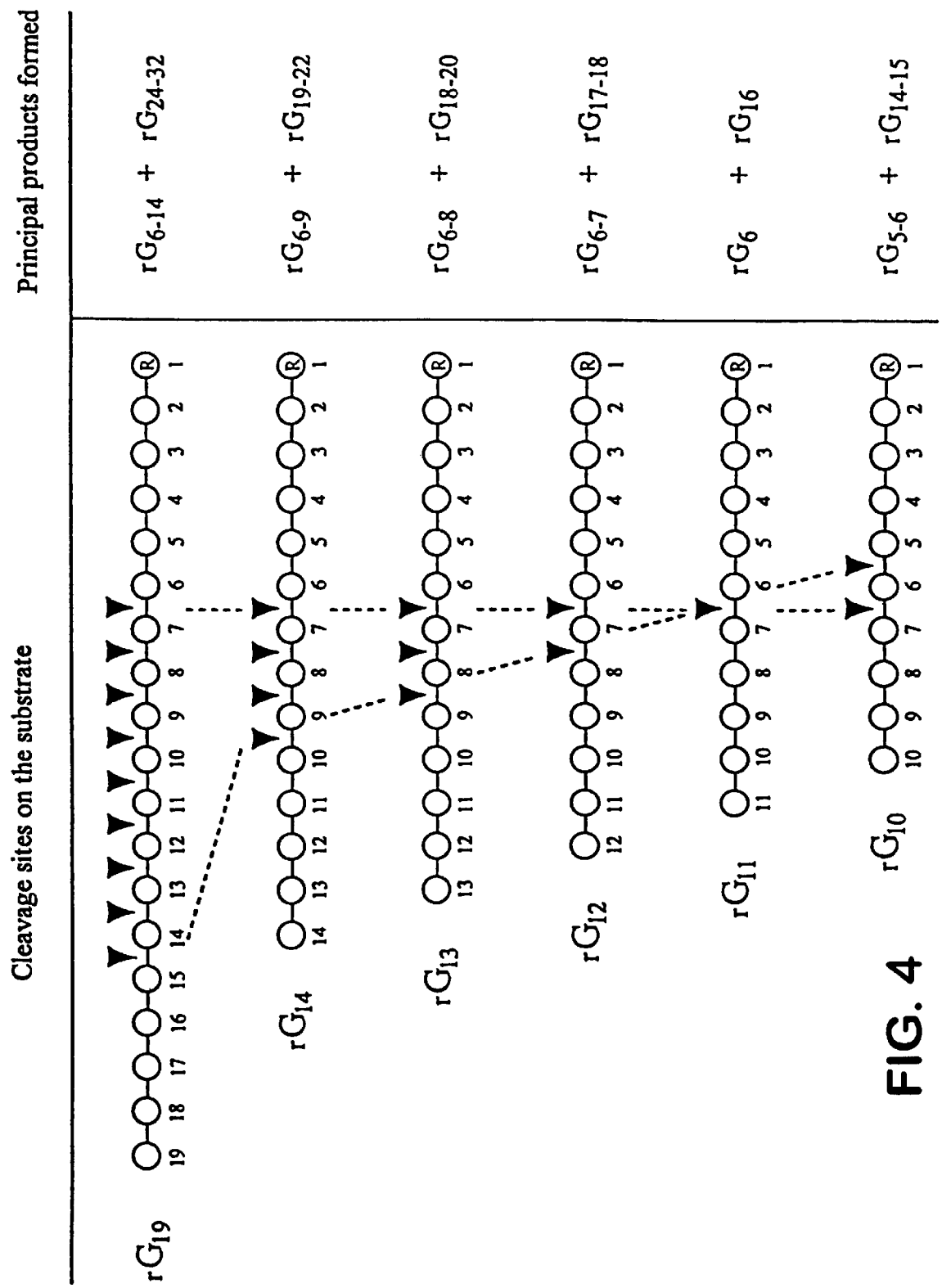

In order to determine the smallest laminarioligosaccharide which could act as acceptor, the purified transferase was incubated with 4 mM of $rG_{11}$ as donor and 16 mM of $rG_8$ or smaller as acceptor. Analyses of the incubations of $rG_{11}$ $rG_4$ or smaller showed the formation of $rG_6$ and $rG_{16}$ as the only initial major products, showing that only $rG_{11}$ had been used as acceptor. However, incubations containing $rG_{11}$ and $rG_5$ to $rG_8$ showed additional transferase products consistent with the use of the latter oligosaccharides as acceptors. For example, the reaction of $rG_{11}$ and $rG_7$ led to the initial formation of $rG_6$, $rG_{12}$ and $rG_{16}$ consistent with:

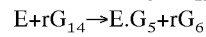
E+$rG_{14}$→E.$G_5$+$rG_6$
E.$G_5$+$rG_{11}$→E+$rG_{16}$
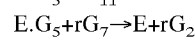
E.$G_5$+$rG_7$→E+$rG_2$ The relative rate of the reaction with the acceptors was determined by using 2 mM of $rG_{11}$ as donor and 32 mM of reduced acceptor marked with ³H and measuring the formation of marked transferase product (FIG. 4). Under these conditions, the reaction with $rG_{11}$ used as acceptor was negligible. The reaction rate increased with an increase in chain length, showing that the 49 kDa enzyme prefers the larger laminarioligosaccharides acceptors.

The transferase showed no activity towards the gentiooligosaccharides (size $G_{3-8}$), chitohexaose, cellopentaose or maltoheptaose, either in the presence or absence of $rG_{11}$, suggesting that the enzyme exclusively uses a β-(1-3) glucan as donor. This was demonstrated by using a reduced branched $G_{10}$ ($rG_{10}$*) similar to the laminaridecaose, except that the sixth link from the reduced end is a β-(1-6)-type link. Incubation of the 49 kDa enzyme with 8mM of $rG_{10}$* gave no products, showing that it was not a donor. However, a similar incubation in the presence of 2 mM of $rG_{11}$ led to the formation of $rG_6$ and an elution peak in the position of $rG_{15}$ as initial major products, showing that $rG_{10}$* can act as an acceptor.

Example 3

¹H NMR Analysis of the Reduced $G_{16}$ Transferase Product

In order to determine if the 49 kDa transferase had produced a new type of bond during the transfer, the product $rG_{16}$ of the transferase was purified from the incubation medium of the transferase with $rG_{11}$. Approximately 300 μg of the product were analyzed by ¹H NMR The ID spectrum of the product $rG_{16}$ of the transferase showed three chemical shifts in the anomeric region:

δ=4.68 ppm corresponding to the glucose residue linked to the glucitol group;

δ=4.75 ppm corresponding to the glucose residue of the non-reduced end;

δ=4.80 ppm corresponding to the intrachain residues of glucose, linked β-(1-3).

The relative intensities of the anomeric signals showed 1, 1 and 13 protons respectively. Since the glucitol gives no signals in the anomeric region, this confirms the length of the oligosaccharide (16 residues), The coupling constants measured for these signals were in agreement with β-linked glucose residues ($^3J_{1,2}$=7.9 Hz). The presence of a single unit of the glucose type at the non-reduced end indicates that the 49 kDa protein had been transferred to the non-reduced end of the β-(1-3) glucan acceptor.

The 1D spectrum of the product $rG_{16}$ was identical, except for the relative intensity of the 4.80 ppm signal compared to that of the $rG_{10}$ laminarioligosaccharide standard. In addition, no chemical shift characteristic of a glucose residue linked (1-2), (1-4) or (1-6) was visible, confirming that the $rG_{16}$ product was a laminarihexadecaose. The conjoint elution of the $rG_{16}$ product with the $rG_{16}$ reference on HPAEC and the insolubility of the larger product are in agreement with the production of a β-(1-3)-type bond during the transfer.

Example 4

Effect of Substrate Concentration on the Reaction Products

In order to determine whether the concentration decreasing of acceptors stimulated the hydrolysis reactions, the 49 kDa transferase was incubated with 3 μl of [$^3$H]-$rG_{11}$ and decreasing quantities of unmarked $rG_{11}$. A shift from the transfer (i) to the hydrolysis (ii) was observed (FIG. 5, inset):

E+[$^3$H]-$rG_{11}$→E.$G_5$+[$^3$H]-$rG_6$ (i)→E.$G_5$+[$^3$H]-$rG_{11}$→E+[$^3$H]-$rG_{16}$ (ii)→E.$G_5$+$H_2O$→E+$G_5$

Figure 5:
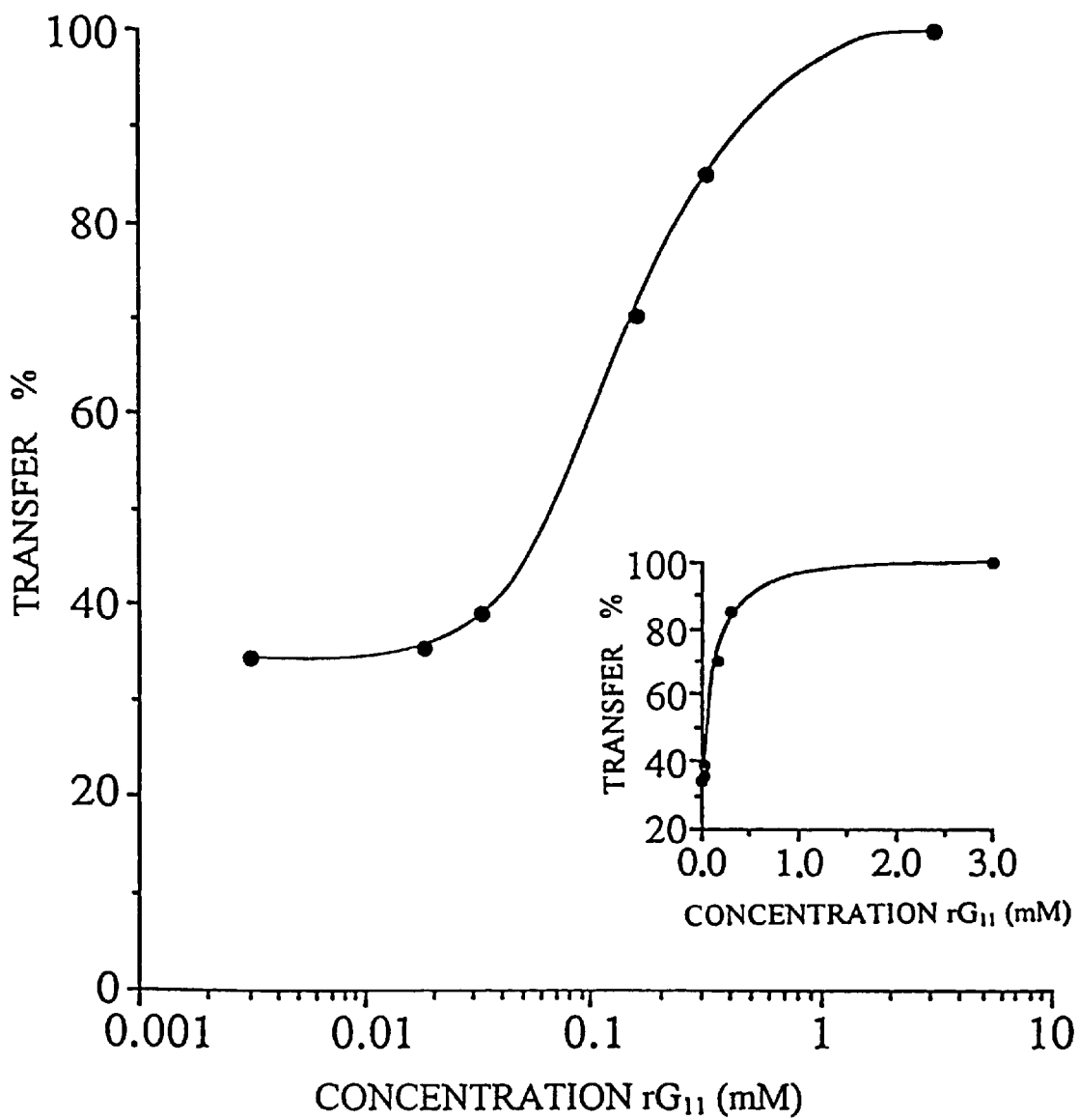

The percentage of transfer was determined by measuring the formation of marked $rG_{16}$ (transfer only) compared with that of marked $rG_6$ (transfer plus hydrolysis) in the reaction. At an $rG_{11}$ concentration of 3 mM, only transfer was detected. As the substrate concentration reduced to 18 μM, the percentage of transfer leveled out at about 35% and did not decrease significantly with a low substrate concentration (3 μM) (FIG. 5). Reduction of the buffer concentration to 10 mM did not change the transfer percentage for any substrate concentration. It seems that below the given conditions, the 49 kDa transferase was unable to catalyze more than about 65% of hydrolysis by simply reducing the substrate concentration to very low levels.

Example 5

Optimum pH and Stability

Figure 6:
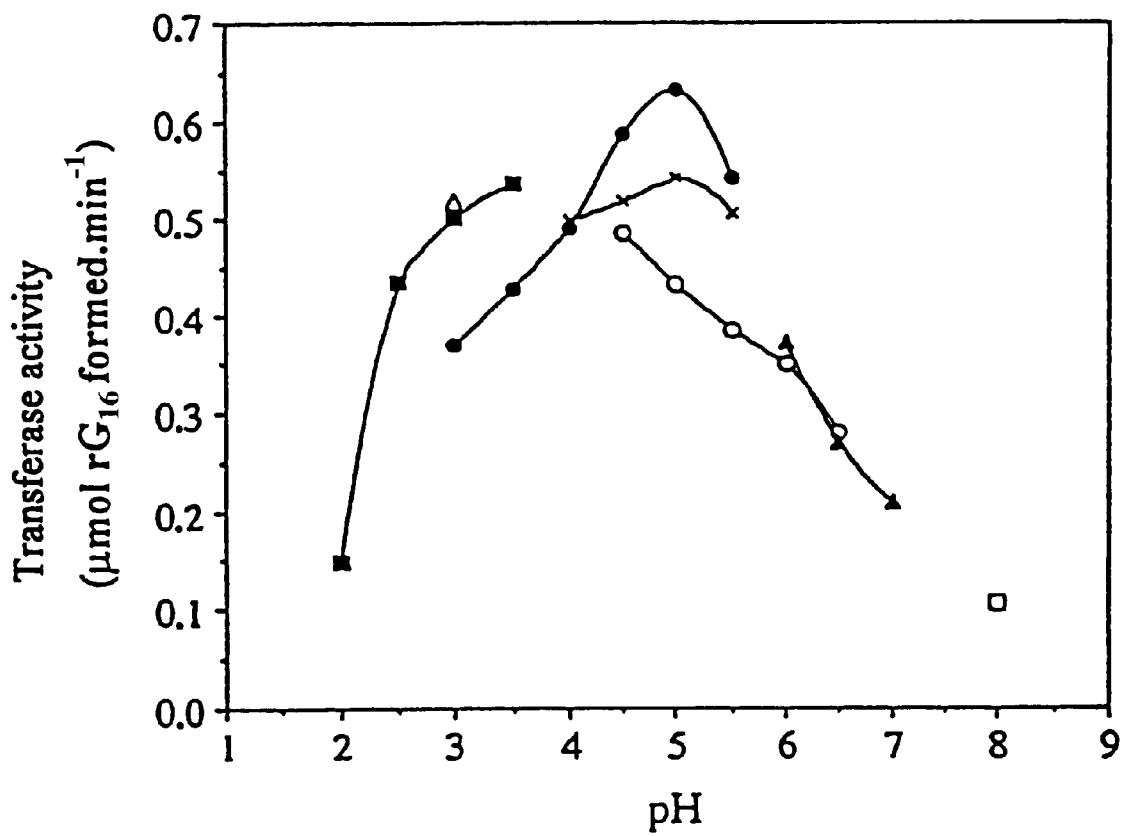
Figure 8:
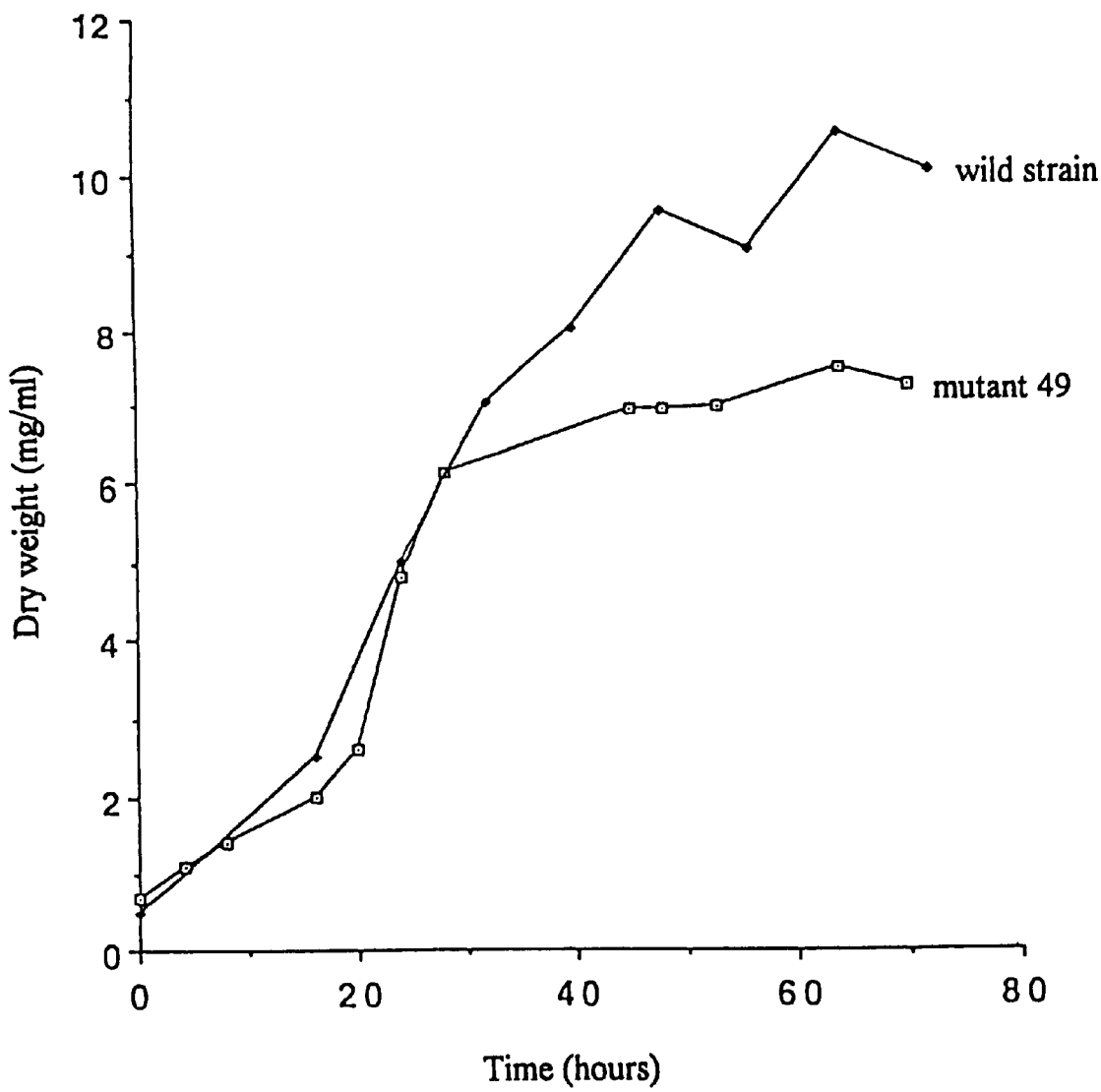
FIG. 8 shows the growth rate of mutant 49 compared to that of the wild strain. Where a pH value is stated, the culture was performed at controlled pH (4 or 7).
Figure 9:
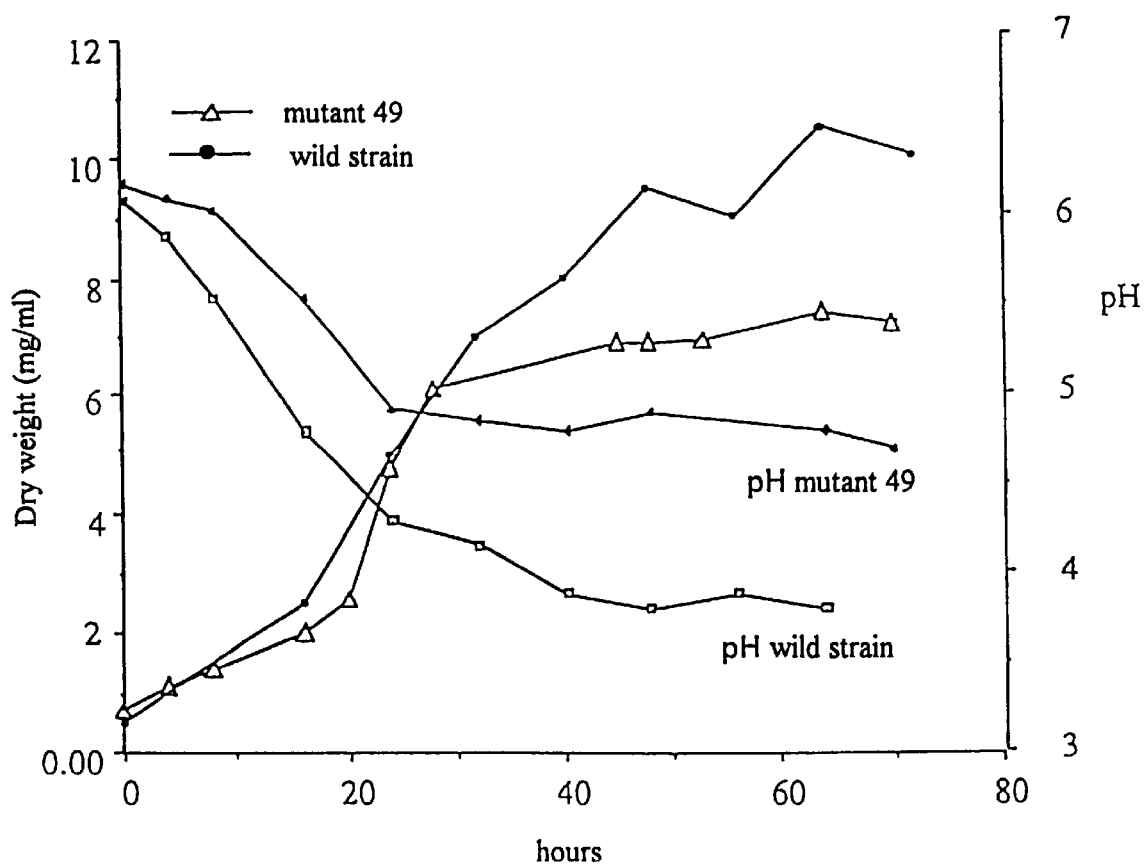
FIG. 9 illustrates the growth of the wild strain and that of the mutant Δ49 and the variation of the pH of the culture medium during the growth of the two strains.

The 49 kDa enzyme was tested at different pH values, the storage stability was verified and the activity of the N-glycosylated enzyme was tested. The enzyme was active over a wide range of acid pH, showing an activity of more than 50% of its maximum between pH 2.5 and 6.0. The enzyme showed a pH optimum of about 5.0 in citrate buffer (FIG. 6). The enzyme was very stable and could be stored at 4° C. in 10 mM citrate buffer, pH 5.0 for several weeks, or dried by a speed-vac and then re-suspended in a buffer, or stored at −20° C. without significant loss of activity. The 44 kDa de-N-glycosylated enzyme prepared under non-denaturing conditions was as active as the native glycosylated enzyme when incubated with 8 nM of $rG_{11}$.

Example 6

Kinetic Analysis

The 49 kDa enzyme catalyzed its transferase-type reaction by a bi-reaction type mechanism (two steps) with an initial hydrolysis of the substrate to liberate the portion of the reduced end, and a subsequent transfer of the remainder of the non-reduced end to a substrate molecule playing the role of an acceptor molecule.

By using $rG_{11}$ as substrate, it was impossible to calculate an apparent Km corresponding to the two steps of the reaction. In order to determine a Km for the donor site, we used an acceptor which was not a donor. We used. [$^3$H]-$rG_7$ (1×10$^6$ cpm) as acceptor at a high concentration (64 mM) with different concentrations of $rG_{11}$ kept below 8 mM. Under these conditions, the reaction took place with $rG_{11}$ as donor and $rG_7$ was used rather than $rG_{11}$ as acceptor, as determined by the absence of formation of the transferase product $rG_{16}$. The initial reaction rate was determined by measuring the appearance of marked $rG_{12}$.

An apparent Km of 5.3 mM was obtained from reciprocal double spots (value of $r^2$=0.997).

Example 7

Cloning, Sequencing and Interruption of the Gene Coding for BGT2 in A. fumigatus.

Two amino acid sequences were obtained from the purified BGT2 protein. The $NH_2$ terminal sequence was DVT-PITVKGNAFFKGDERFY (SEQ ID NO: 20) and an internal sequence was DAPNWDVDNDALP (SEQ ID NO: 21). An oligonucleotide of 38 units on the N-terminal part having the following sequence SEQ ID No 4:

(AAG GG(T/C) AA(C/T) GC(T/C) TTC TT(C/T) AAG GG(T/C) GA(T/C) GAG CG(T/C) TTC TA)

was used to screen a gene bank created in the phage EMBL3 after partial digestion by Sau3A of the DNA of A. fumigatus as described by Monod (1994, 33–40, Mol. Biology of pathogenic fungi, B. Maresca and G. S. Kobayashi).

The transfer was performed on membranes of the ZETAPROBE type. The membranes were pre-hybridized and hybridized at 50° C. in a solution containing SSC 5×, $Na_2HPO_4$ 25 mM, pH7, SDS 7%, Denhard 10× and 1% salmon sperm. The membranes were washed twice at 42° C. in a solution containing SSC 3×, Denhard 10×, SDS 5%, $Na_2HPO_4$ 25 mM, and twice in an SDS solution with 1% SSC 1×.

The cloning and sequencing of the gene coding for the BGT2 protein showed significant homologies with the genes PHR1 and GAS1 previously identified in C. albicans and S. cerevisiae respectively (Saporito Irwin and Coil. (1995) Mol. Cell Biol., 15, 601–613; Nuoffer and Coil., J. Biol. Chem., (1991), 226, 19, 12242–12248) (FIG. 7). The GAS 1 gene from S. cerevisiae was also responsible for a glucanosyl transferase activity. In this fungus species, the minimum size of optimal substrate was G10, rather than G11 for A. fumigatus.

The disruption of the BGT2 gene was carried out by using the vector pAN7-1 (Punt and Coil. (1987) Gene 56, 117–124) supplied by P. Punt (TNO, Rijinsik). This vector was modified as pN4 (Paris and Coil. (1993) FEMS Microbiol. Lett. 111, 31–36) by the replacement of a restriction site HindIII by a Sma1 site. About 50% of the open reading frame of BGT2 was replaced by pN4 at an EcoRV restriction site. A complete transformation was performed as previously described (Paris, (1994) Isolation of protease negative mutants of Aspergillus fumigatus by insertion of a disrupted gene, p. 49–55. Mol. Biology of pathogenic fungi, B. Maresca and G. S. Kobayashi) by using protoplasts produced by Novozyme and the linearized plasmid in the presence of PEG.

The Δ49 mutant from A. fumigatus obtained was deposited on Jul. 30, 1996 at the CNCM under the deposit number I-1764.

It showed no phenotype distinct from the wild strain, except for a total inhibition of the growth in the fermenter after 24 hours growth.

Example 8

Cloning and Sequencing of the cDNA of BGT2.

The cDNA of BGT2 was obtained by amplification with two primers of cDNA type 5' GAATTCGACGACGT-TACTCCCATCACT 3' (SEQ ID NO: 5) of P1 and 5' TCTAGAGGGTATGAGAAGAACAAATCA 3' (SEQ ID NO: 6) of P2 obtained from 10 ng of cDNA, 1U of taq polymerase, 200 mM of each primer. 30 Amplification cycles were performed, comprising 1 minute at 95° C., one minute at 55° C. and one minute at 72° C.

The amplified preparation was then cloned in a vector using a TA Cloning kit (In Vitrogen).

Example 9

Expression of the β-(1-3)-glucanosyltransferase

Experiments using Triton X114 divisions with or without treatment with GPI-phospholipase C showed that the protein BGT2 from A. fumigatus was attached to the plasma membrane by a GPI residue.

The attachment of the protein to the membrane was not necessary for retention of enzymatic activity. We showed that in A. fumigatus the same activity was present when the protein was either free in the culture medium (in the absence of the GPI bond) or attached to the plasma membrane.

These results suggested that the expression of the glucanosyltransferase could be performed in vectors by a secreted expression. The Pichia pastoris expression system from In Vitrogen was selected. This system had been previously used for another 88 kDA protein from A. fumigatus and it was confirmed that Pichia preserved the glycosylation site of the native protein very well.

The vector used was pPICZα (In Vitrogen) for the secretion with a myc epitope and six histidine residues in tandem for easy purification. The C-terminal sequence responsible for the attachment by GPI was removed before the subcloning in pPICZα so as to obtain an enzymatically active truncated secreted protein.

This recombinant protein was used for the detection of antifungal drugs. The inhibition of the enzymatic activity may be measured by an HPLC-type detection in the absence of cleavage and an additional elongation of any β-(1-3) laminarioligosaccharides with dp>10 in the presence of p49 from A. fumigatus.

The absence of motility of the laminarioligosaccharide measured by thin-layer chromatography by conventional techniques or directly after marking of the reduced end with a chromogenic or fluorogenic radical could be a fundamental technique for performing detection automatically.

Since the product from the β-(1-3) glucanosyltransferase becomes insoluble in an aqueous medium, because of the elongation of the β-glucan chain, the absence of precipitation of any product after prolonged incubation using a radioactively marked substrate could also be used for drug detection.

Example 10

Identification of Genes with Homologies with BGT2

Degenerate oligonucleotide primers corresponding to the regions retained in the sequence in FIG. 10 were synthesized by GENSET. They had the following sequences:

SEQ ID No 7 (P3): 5' GSYTTCTTCKCYGGCAAC-GAGGTT 3'

SEQ ID No 8 (P4'): 5' GTTGCAGCCGWATTCG-GASAYGAA 3' in which Y is C or T

K is T or G

S is C or G

W is A or T.

PCR reactions were carried out in a volume of 100 μl containing 1.5 mM MgCl$_2$, 50 mM KCl, 10 mM TrisCl (pH 8), 250 μM of dATP, dGTP, dCTP and dTTP (Pharmacia), 1 μM of each primer, 2.5 units of AMPLITAQ DNA polymerase (Pharmacia) and 50 ng of genomic DNA. The amplification was performed in an OmniGene apparatus initially for 5 min at 93° C., then for 30 cycles of 1 min at 93° C., then for 1 min at 50° C. and 1 min at 72° C. The products from the PCR reaction were analyzed by electrophoresis on 1% agarose gel, then revealed by ultraviolet after coloration with ethidium bromide.

The fragments resulting from the PCR reaction were ligatured in pCR2.1 (TA cloning kit, In Vitrogen). The recombinant plasmid inserts were sequenced by the dideoxy chain termination method (Sanger et al., 1977) using SEQUENASE, Version 2 (US Biochemicals) according to the manufacturer's instructions.

Two nucleotide sequences were thus amplified: sequences SEQ ED No 9 and SEQ ID No 11. The amino acid sequences deduced from the nucleotide sequences were sequences SEQ ID No 10 and SEQ ID No 12, corresponding to the genes named BGT4 and BGT3.

These sequences are in particular described in the list below. They have identity percentages with BGT2 of 41% and 37% respectively.

Figure 11:
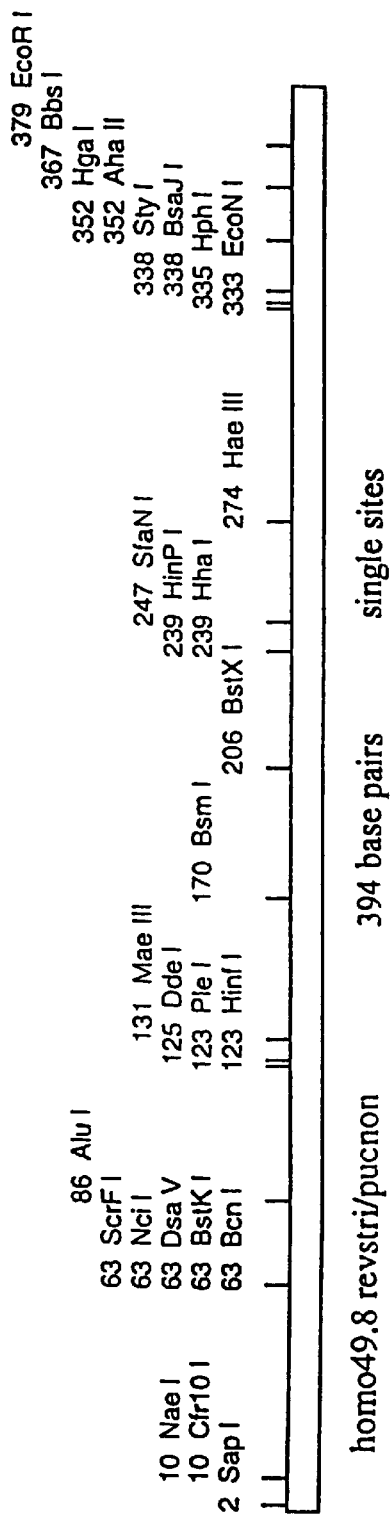
FIGS. 11 and 12 are restriction maps of the sequences of the genes homologous with the BGT2 gene, named BGT4 and BGT3 respectively.
Figure 12:
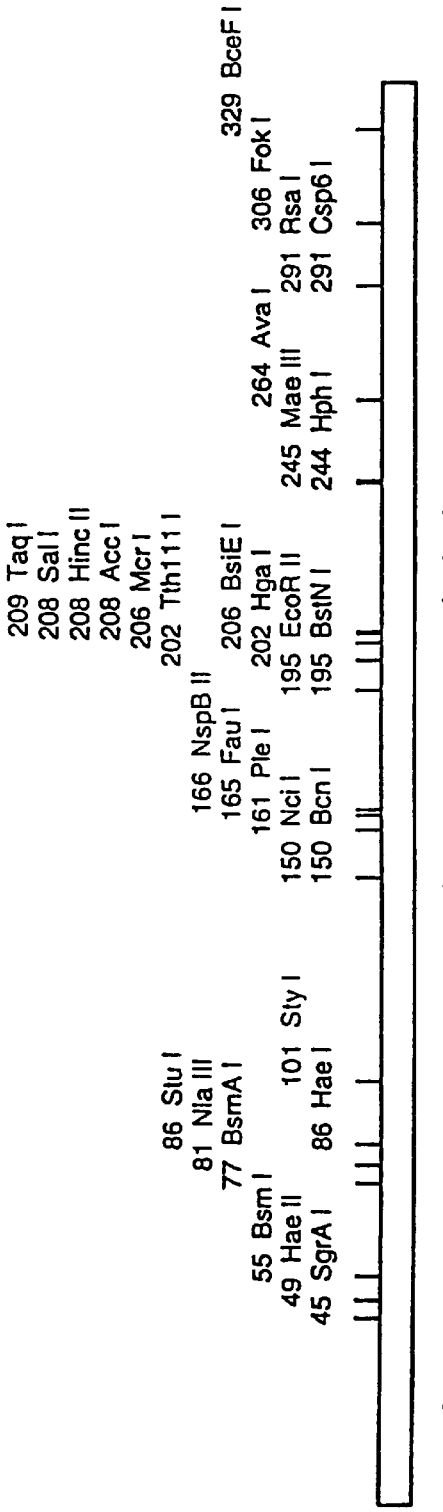

Restriction maps of the two sequences SEQ ID No 10 and SEQ ID No 12 are represented respectively in FIGS. 12 and 11.

The sequences SEQ ID No 9 and SEQ ID No 11 were inserted into the plasmid PCRII which was introduced into E. coli. These bacteria were deposited on the Aug. 22, 1997 at the CNCM under numbers I-1914 and I-1913 respectively.

TABLE

Reaction of the transferase with an initial rate of formation of the transfer product

| Transferase reaction | Transfer rate (nmol.min$^{-1}$.mg protein$^{-1}$) |
|---|---|
| rG$_{11}$ + [$^3$H]-rG$_5$ → RG$_6$ + [$^3$H]-rG$_{10}$ | 203 |
| rG$_{11}$ + [$^3$H]-rG$_6$ → RG$_6$ + [$^3$H]-rG$_{11}$ | 387 |
| rG$_{11}$ + [$^3$H]-rG$_7$ → RG$_6$ + [$^3$H]-rG$_{12}$ | 484 |
| rG$_{11}$ + [$^3$H]-rG$_8$ → RG$_6$ + [$^3$H]-rG$_{13}$ | 586 |

What is claimed is:

1. An isolated protein having β-(1-3)-glycanosyltransferase type activity, wherein the protein has at least 50% homology with a protein comprising SEQ ID NO:3.

2. The protein according to claim 1, wherein the protein comprises at least one site for N-linked glycosylation.

3. The protein according to claim 1, wherein the protein exhibits a molecular weight of 49 kD.

4. The protein according to claim 1, wherein the protein is attached to a plasma membrane by a glycosylphosphatidylinositol radical.

5. The protein according to claim 1, wherein said protein has at least 60% homology with a protein comprising SEQ ID NO:3.

6. The protein according to claim 5, wherein said protein has at least 85% homology with a protein comprising SEQ ID NO:3.

7. The protein according to claim 1, wherein the protein exhibits a molecular weight of 44 kD.

8. A polypeptide fragment having β-(1-3)-glycanosyltransferase type activity of the protein according to any one of claims 1–4.

* * * * *

UNITED STATES PATENT AND TRADEMARK OFFICE
CERTIFICATE OF CORRECTION

PATENT NO.   : 6,551,811 B1
DATED        : April 22, 2003
INVENTOR(S)  : Thierry Fontaine et al.

It is certified that error appears in the above-identified patent and that said Letters Patent is hereby corrected as shown below:

<u>Column 48,</u>
Line 66, "claims 1-4." should read -- claims 1-7. --

Signed and Sealed this

Twelfth Day of August, 2003

JAMES E. ROGAN
*Director of the United States Patent and Trademark Office*

SEQUENCE LISTING

<160> NUMBER OF SEQ ID NOS: 21

<210> SEQ ID NO 1
<211> LENGTH: 1359
<212> TYPE: DNA
<213> ORGANISM: Aspergillus fumigatus
<220> FEATURE:
<221> NAME/KEY: CDS
<222> LOCATION: (1)..(1356)

<400> SEQUENCE: 1

```
atg aag gcc tct gct gtt act gcc gct ctc gcc gtc ggt gct tcc acc        48
Met Lys Ala Ser Ala Val Thr Ala Ala Leu Ala Val Gly Ala Ser Thr
 1               5                  10                  15 gtt ctg gca gcc ccc tcc atc aag gct cgt gac gac gtt act ccc atc        96
Val Leu Ala Ala Pro Ser Ile Lys Ala Arg Asp Asp Val Thr Pro Ile
             20                  25                  30 act gtc aag ggc aat gcc ttc ttc aag ggc gat gag cgt ttc tat att       144
Thr Val Lys Gly Asn Ala Phe Phe Lys Gly Asp Glu Arg Phe Tyr Ile
         35                  40                  45 cgc ggt gtc gac tac cag ccc ggt ggc tcc tcc gac ctg gct gat ccc       192
Arg Gly Val Asp Tyr Gln Pro Gly Gly Ser Ser Asp Leu Ala Asp Pro
     50                  55                  60 atc gct gat gcc gat ggt tgc aag cgt gac att gcc aag ttc aag gag       240
Ile Ala Asp Ala Asp Gly Cys Lys Arg Asp Ile Ala Lys Phe Lys Glu
 65                  70                  75                  80 ctg ggc ctg aac act atc cgt gtc tac tcg gtc gac aac tcc aag aac       288
Leu Gly Leu Asn Thr Ile Arg Val Tyr Ser Val Asp Asn Ser Lys Asn
                 85                  90                  95 cac gat gag tgt atg aat aca ctg gct gat gct ggc atc tat ctg gtg       336
His Asp Glu Cys Met Asn Thr Leu Ala Asp Ala Gly Ile Tyr Leu Val
            100                 105                 110 ctc gat gtc aac act ccc aag tac tcc atc aac cgc gcc aag cct aag       384
Leu Asp Val Asn Thr Pro Lys Tyr Ser Ile Asn Arg Ala Lys Pro Lys
        115                 120                 125 gag tcg tac aac gat gtc tac ctc cag tat atc ttc gct acc gtt gat       432
Glu Ser Tyr Asn Asp Val Tyr Leu Gln Tyr Ile Phe Ala Thr Val Asp
    130                 135                 140 gct ttc gcc ggt tac aag aac acc ctc gct ttc ttc tcc ggc aac gag       480
Ala Phe Ala Gly Tyr Lys Asn Thr Leu Ala Phe Phe Ser Gly Asn Glu
145                 150                 155                 160 gtt atc aac gat ggc cct tcc tcc tct gct gct ccc tac gtc aag gcc       528
Val Ile Asn Asp Gly Pro Ser Ser Ser Ala Ala Pro Tyr Val Lys Ala
                165                 170                 175 gtc act cgt gat ctg cgt cag tac atc cgt agc cgc aag tac cgt gag       576
Val Thr Arg Asp Leu Arg Gln Tyr Ile Arg Ser Arg Lys Tyr Arg Glu
            180                 185                 190 att cct gtc ggc tac tcg gct gcc gat atc gac acc aac cgt ctt cag       624
Ile Pro Val Gly Tyr Ser Ala Ala Asp Ile Asp Thr Asn Arg Leu Gln
        195                 200                 205 atg gcc cag tat atg aac tgc ggt tcc gac gac gag cgc agt gac ttc       672
Met Ala Gln Tyr Met Asn Cys Gly Ser Asp Asp Glu Arg Ser Asp Phe
    210                 215                 220 ttc gct ttc aac gac tac tcc tgg tgc gat ccc tcc tct ttc aaa acc       720
Phe Ala Phe Asn Asp Tyr Ser Trp Cys Asp Pro Ser Ser Phe Lys Thr
225                 230                 235                 240 tcg ggc tgg gat cag aag gtc aag aac ttc act ggc tac ggt ctt cct       768
Ser Gly Trp Asp Gln Lys Val Lys Asn Phe Thr Gly Tyr Gly Leu Pro
                245                 250                 255
```

```
ctc ttc ctg tcc gaa tac ggc tgc aac acc aac aag cgt caa ttc caa      816
Leu Phe Leu Ser Glu Tyr Gly Cys Asn Thr Asn Lys Arg Gln Phe Gln
            260                 265                 270 gaa gtc agc tct ctc tac tcc acg gac atg act ggt gtc tac tct ggt      864
Glu Val Ser Ser Leu Tyr Ser Thr Asp Met Thr Gly Val Tyr Ser Gly
                275                 280                 285 ggt ctc gtg tac gag tac tct cag gag gcc agc aac tac ggt ctg gtg      912
Gly Leu Val Tyr Glu Tyr Ser Gln Glu Ala Ser Asn Tyr Gly Leu Val
        290                 295                 300 gag att agc ggc aac aat gtc aag gag ctc cca gac ttc gac gct ctg      960
Glu Ile Ser Gly Asn Asn Val Lys Glu Leu Pro Asp Phe Asp Ala Leu
305                 310                 315                 320 aag acc gcg ttc gaa aag acc tcc aac ccc tcc ggc gac ggc aac tac     1008
Lys Thr Ala Phe Glu Lys Thr Ser Asn Pro Ser Gly Asp Gly Asn Tyr
                325                 330                 335 aac aag act ggt ggt gcc aac cct tgc ccc gct aag gac gct ccc aac     1056
Asn Lys Thr Gly Gly Ala Asn Pro Cys Pro Ala Lys Asp Ala Pro Asn
            340                 345                 350 tgg gac gtt gac aac gat gct ctt cct gcc atc ccc gag ccc gcc aag     1104
Trp Asp Val Asp Asn Asp Ala Leu Pro Ala Ile Pro Glu Pro Ala Lys
        355                 360                 365 aag tac atg act gag ggt gct ggc aag ggc cct ggt ttt gcc gga cct     1152
Lys Tyr Met Thr Glu Gly Ala Gly Lys Gly Pro Gly Phe Ala Gly Pro
370                 375                 380 ggc agc cag gac cgt ggt acc cag tcc act gcc act gct gag ccc gga     1200
Gly Ser Gln Asp Arg Gly Thr Gln Ser Thr Ala Thr Ala Glu Pro Gly
385                 390                 395                 400 tct ggc tct gcc act gga agc agc agc agc ggc acc tcc acc tct tcc     1248
Ser Gly Ser Ala Thr Gly Ser Ser Ser Ser Gly Thr Ser Thr Ser Ser
                405                 410                 415 aag ggc gct gca gct ggc ctg act gtc cct agc ctg acc atg gct ccc     1296
Lys Gly Ala Ala Ala Gly Leu Thr Val Pro Ser Leu Thr Met Ala Pro
            420                 425                 430 gtt gtc gtt ggt gcg gtt aca ctc ctg tcc acc gtc ttc ggc gct ggc     1344
Val Val Val Gly Ala Val Thr Leu Leu Ser Thr Val Phe Gly Ala Gly
        435                 440                 445 ctc gtc ctc ttg tga                                                  1359
Leu Val Leu Leu
    450

<210> SEQ ID NO 2
<211> LENGTH: 452
<212> TYPE: PRT
<213> ORGANISM: Aspergillus fumigatus

<400> SEQUENCE: 2

Met Lys Ala Ser Ala Val Thr Ala Ala Leu Ala Val Gly Ala Ser Thr
  1               5                  10                  15

Val Leu Ala Ala Pro Ser Ile Lys Ala Arg Asp Asp Val Thr Pro Ile
               20                  25                  30

Thr Val Lys Gly Asn Ala Phe Phe Lys Gly Asp Glu Arg Phe Tyr Ile
           35                  40                  45

Arg Gly Val Asp Tyr Gln Pro Gly Gly Ser Ser Asp Leu Ala Asp Pro
       50                  55                  60

Ile Ala Asp Ala Asp Gly Cys Lys Arg Asp Ile Ala Lys Phe Lys Glu
 65                  70                  75                  80

Leu Gly Leu Asn Thr Ile Arg Val Tyr Ser Val Asp Asn Ser Lys Asn
                 85                  90                  95
```

His Asp Glu Cys Met Asn Thr Leu Ala Asp Ala Gly Ile Tyr Leu Val
                100                 105                 110

Leu Asp Val Asn Thr Pro Lys Tyr Ser Ile Asn Arg Ala Lys Pro Lys
        115                 120                 125

Glu Ser Tyr Asn Asp Val Tyr Leu Gln Tyr Ile Phe Ala Thr Val Asp
        130                 135                 140

Ala Phe Ala Gly Tyr Lys Asn Thr Leu Ala Phe Phe Ser Gly Asn Glu
145                 150                 155                 160

Val Ile Asn Asp Gly Pro Ser Ser Ala Ala Pro Tyr Val Lys Ala
        165                 170                 175

Val Thr Arg Asp Leu Arg Gln Tyr Ile Arg Ser Arg Lys Tyr Arg Glu
        180                 185                 190

Ile Pro Val Gly Tyr Ser Ala Ala Asp Ile Asp Thr Asn Arg Leu Gln
        195                 200                 205

Met Ala Gln Tyr Met Asn Cys Gly Ser Asp Asp Glu Arg Ser Asp Phe
        210                 215                 220

Phe Ala Phe Asn Asp Tyr Ser Trp Cys Asp Pro Ser Ser Phe Lys Thr
225                 230                 235                 240

Ser Gly Trp Asp Gln Lys Val Lys Asn Phe Thr Gly Tyr Gly Leu Pro
                245                 250                 255

Leu Phe Leu Ser Glu Tyr Gly Cys Asn Thr Asn Lys Arg Gln Phe Gln
                260                 265                 270

Glu Val Ser Ser Leu Tyr Ser Thr Asp Met Thr Gly Val Tyr Ser Gly
        275                 280                 285

Gly Leu Val Tyr Glu Tyr Ser Gln Glu Ala Ser Asn Tyr Gly Leu Val
        290                 295                 300

Glu Ile Ser Gly Asn Asn Val Lys Glu Leu Pro Asp Phe Asp Ala Leu
305                 310                 315                 320

Lys Thr Ala Phe Glu Lys Thr Ser Asn Pro Ser Gly Asp Gly Asn Tyr
                325                 330                 335

Asn Lys Thr Gly Gly Ala Asn Pro Cys Pro Ala Lys Asp Ala Pro Asn
                340                 345                 350

Trp Asp Val Asp Asn Asp Ala Leu Pro Ala Ile Pro Glu Pro Ala Lys
        355                 360                 365

Lys Tyr Met Thr Glu Gly Ala Gly Lys Gly Pro Gly Phe Ala Gly Pro
        370                 375                 380

Gly Ser Gln Asp Arg Gly Thr Gln Ser Thr Ala Thr Glu Pro Gly
385                 390                 395                 400

Ser Gly Ser Ala Thr Gly Ser Ser Ser Gly Thr Ser Thr Ser Ser
                405                 410                 415

Lys Gly Ala Ala Ala Gly Leu Thr Val Pro Ser Leu Thr Met Ala Pro
                420                 425                 430

Val Val Val Gly Ala Val Thr Leu Leu Ser Thr Val Phe Gly Ala Gly
        435                 440                 445

Leu Val Leu Leu
    450

<210> SEQ ID NO 3
<211> LENGTH: 426
<212> TYPE: PRT
<213> ORGANISM: Aspergillus fumigatus

<400> SEQUENCE: 3

Asp Asp Val Thr Pro Ile Thr Val Lys Gly Asn Ala Phe Phe Lys Gly
1               5                   10                  15

-continued

```
Asp Glu Arg Phe Tyr Ile Arg Gly Val Asp Tyr Gln Pro Gly Gly Ser
            20                  25                  30

Ser Asp Leu Ala Asp Pro Ile Ala Asp Ala Asp Gly Cys Lys Arg Asp
        35                  40                  45

Ile Ala Lys Phe Lys Glu Leu Gly Leu Asn Thr Ile Arg Val Tyr Ser
    50                  55                  60

Val Asp Asn Ser Lys Asn His Asp Glu Cys Met Asn Thr Leu Ala Asp
65                  70                  75                  80

Ala Gly Ile Tyr Leu Val Leu Asp Val Asn Thr Pro Lys Tyr Ser Ile
                85                  90                  95

Asn Arg Ala Lys Pro Lys Glu Ser Tyr Asn Asp Val Tyr Leu Gln Tyr
            100                 105                 110

Ile Phe Ala Thr Val Asp Ala Phe Ala Gly Tyr Lys Asn Thr Leu Ala
        115                 120                 125

Phe Phe Ser Gly Asn Glu Val Ile Asn Asp Gly Pro Ser Ser Ser Ala
    130                 135                 140

Ala Pro Tyr Val Lys Ala Val Thr Arg Asp Leu Arg Gln Tyr Ile Arg
145                 150                 155                 160

Ser Arg Lys Tyr Arg Glu Ile Pro Val Gly Tyr Ser Ala Ala Asp Ile
                165                 170                 175

Asp Thr Asn Arg Leu Gln Met Ala Gln Tyr Met Asn Cys Gly Ser Asp
            180                 185                 190

Asp Glu Arg Ser Asp Phe Phe Ala Phe Asn Asp Tyr Ser Trp Cys Asp
        195                 200                 205

Pro Ser Ser Phe Lys Thr Ser Gly Trp Asp Gln Lys Val Lys Asn Phe
    210                 215                 220

Thr Gly Tyr Gly Leu Pro Leu Phe Leu Ser Glu Tyr Gly Cys Asn Thr
225                 230                 235                 240

Asn Lys Arg Gln Phe Gln Glu Val Ser Ser Leu Tyr Ser Thr Asp Met
                245                 250                 255

Thr Gly Val Tyr Ser Gly Gly Leu Val Tyr Glu Tyr Ser Gln Glu Ala
            260                 265                 270

Ser Asn Tyr Gly Leu Val Glu Ile Ser Gly Asn Asn Val Lys Glu Leu
        275                 280                 285

Pro Asp Phe Asp Ala Leu Lys Thr Ala Phe Glu Lys Thr Ser Asn Pro
    290                 295                 300

Ser Gly Asp Gly Asn Tyr Asn Lys Thr Gly Gly Ala Asn Pro Cys Pro
305                 310                 315                 320

Ala Lys Asp Ala Pro Asn Trp Asp Val Asp Asn Asp Ala Leu Pro Ala
                325                 330                 335

Ile Pro Glu Pro Ala Lys Lys Tyr Met Thr Glu Gly Ala Gly Lys Gly
            340                 345                 350

Pro Gly Phe Ala Gly Pro Gly Ser Gln Asp Arg Gly Thr Gln Ser Thr
        355                 360                 365

Ala Thr Ala Glu Pro Gly Ser Gly Ser Ala Thr Gly Ser Ser Ser Ser
    370                 375                 380

Gly Thr Ser Thr Ser Ser Lys Gly Ala Ala Ala Gly Leu Thr Val Pro
385                 390                 395                 400

Ser Leu Thr Met Ala Pro Val Val Val Gly Ala Val Thr Leu Leu Ser
                405                 410                 415

Thr Val Phe Gly Ala Gly Leu Val Leu Leu
            420                 425
```

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 4
aagggyaayg cyttcttyaa gggygaygag cgyttcta                               38

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 5
gaattcgacg acgttactcc catcact                                          27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 6
tctagagggt atgagaagaa caaatca                                          27

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 7
gsyttcttck cyggcaacga ggtt                                             24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 8
gttgcagccg wattcggasa ygaa                                             24

<210> SEQ ID NO 9
<211> LENGTH: 394
<212> TYPE: DNA
<213> ORGANISM: Aspergillus fumigatus

<400> SEQUENCE: 9
ggcttcttcg ccggcaacga ggttatcaac gagcagagtg tcaagaacgt tcccacttac      60
gtccgggtat gtcatccatc cccacagctt acgattgcct gtccactgac actctcgtag     120
gcgactcagc gtgacatgaa ggactactac gcaaagaacc ttgaccgcag cattcctgtt     180
ggctattctg ctgccgatat tcgtcccatc ctcatggcac ccctcaacta cttcatgtgc     240
gctgacgatg ctaattccca atcggacttc ttcggcctca actcctactc gtggtgcggc     300

```
aactcgtcct acaccaagag tggctacgat gtcctcacca aggactttgc cgacgcctct      360
atccccgtct tcatctccga attcggctgc aaca                                  394
```

<210> SEQ ID NO 10
<211> LENGTH: 36
<212> TYPE: PRT
<213> ORGANISM: Aspergillus fumigatus

<400> SEQUENCE: 10

```
Gly Phe Phe Ala Gly Asn Glu Val Ile Asn Glu Gln Ser Val Lys Asn
 1               5                  10                  15

Val Pro Thr Tyr Val Arg Val Cys His Pro Ser Pro Gln Leu Thr Ile
            20                  25                  30

Ala Cys Pro Leu
        35
```

<210> SEQ ID NO 11
<211> LENGTH: 339
<212> TYPE: DNA
<213> ORGANISM: Aspergillus fumigatus

<400> SEQUENCE: 11

```
ggtttcttcg ccggcaacga ggttgtgaat caggcgaatc agtccgccgg cgctgcattc       60
gtcaaggccg ccgcgcgaga catgaaggcc tacatcaaga ccaagggata ccggcaatcg      120
ctggcaattg gatacgcgac cactgacaac ccggaaatcc gactcccgct gtccgactac      180
ctcaactgcg gcgaccaggc cgacgcggtc gacttcttcg gctacaacat ctacgaatgg      240
tgcggtgaca agaccttcca gacctcgggc taccagaacc gcaccgagga gtacaaggac      300
tactccatcc ccatcttcat ctccgaatac ggctgcaac                             339
```

<210> SEQ ID NO 12
<211> LENGTH: 113
<212> TYPE: PRT
<213> ORGANISM: Aspergillus fumigatus

<400> SEQUENCE: 12

```
Gly Phe Phe Ala Gly Asn Glu Val Val Asn Gln Ala Asn Gln Ser Ala
 1               5                  10                  15

Gly Ala Ala Phe Val Lys Ala Ala Ala Arg Asp Met Lys Ala Tyr Ile
            20                  25                  30

Lys Thr Lys Gly Tyr Arg Gln Ser Leu Ala Ile Gly Tyr Ala Thr Thr
        35                  40                  45

Asp Asn Pro Glu Ile Arg Leu Pro Leu Ser Asp Tyr Leu Asn Cys Gly
    50                  55                  60

Asp Gln Ala Asp Ala Val Asp Phe Phe Gly Tyr Asn Ile Tyr Glu Trp
65                  70                  75                  80

Cys Gly Asp Gln Thr Phe Gln Thr Ser Gly Tyr Gln Asn Arg Thr Glu
                85                  90                  95

Glu Tyr Lys Asp Tyr Ser Ile Pro Ile Phe Ile Ser Glu Tyr Gly Cys
            100                 105                 110

Asn
```

<210> SEQ ID NO 13
<211> LENGTH: 553
<212> TYPE: PRT
<213> ORGANISM: Saccharomyces cerevisiae -continued

```
<400> SEQUENCE: 13

Met Leu Phe Lys Ser Leu Ser Lys Leu Ala Thr Ala Ala Phe Phe
 1               5                  10                  15

Ala Gly Val Ala Thr Ala Asp Asp Val Pro Ala Ile Glu Val Gly
             20                  25                  30

Asn Lys Phe Phe Tyr Ser Asn Asn Gly Ser Gln Phe Tyr Ile Arg Gly
             35                  40                  45

Val Ala Tyr Gln Ala Asp Thr Ala Asn Glu Thr Ser Gly Ser Thr Val
 50                  55                  60

Asn Asp Pro Leu Ala Asn Tyr Glu Ser Cys Ser Arg Asp Ile Pro Tyr
 65                  70                  75                  80

Leu Lys Lys Leu Asn Thr Asn Val Ile Arg Val Tyr Ala Ile Asn Thr
             85                  90                  95

Thr Leu Asp His Ser Glu Cys Met Lys Ala Leu Asn Asp Ala Asp Ile
            100                 105                 110

Tyr Val Ile Ala Asp Leu Ala Ala Pro Ala Thr Ser Ile Asn Arg Asp
            115                 120                 125

Asp Pro Thr Trp Thr Val Asp Leu Phe Asn Ser Tyr Lys Thr Val Val
            130                 135                 140

Asp Thr Pro Ala Asn Tyr Thr Asn Val Leu Phe Gly Phe Phe Ala Gly
145                 150                 155                 160

Asn Glu Val Thr Asn Asn Tyr Thr Asn Thr Asp Ala Ser Ala Phe Val
                165                 170                 175

Lys Ala Ala Ile Arg Asp Val Arg Gln Tyr Ile Ser Asp Lys Asn Tyr
            180                 185                 190

Arg Lys Ile Pro Val Gly Tyr Ser Ser Asn Asp Asp Glu Asp Thr Arg
            195                 200                 205

Val Lys Met Thr Asp Tyr Phe Ala Cys Gly Asp Asp Val Lys Ala
            210                 215                 220

Asp Phe Tyr Gly Ile Asn Met Tyr Glu Trp Cys Gly Lys Ser Asp Phe
225                 230                 235                 240

Lys Thr Ser Gly Tyr Ala Asp Arg Thr Ala Glu Phe Lys Asn Leu Ser
                245                 250                 255

Ile Pro Val Phe Phe Ser Glu Tyr Gly Cys Asn Glu Val Thr Pro Arg
            260                 265                 270

Leu Phe Thr Glu Val Glu Ala Leu Tyr Gly Ser Asn Met Thr Asp Val
            275                 280                 285

Trp Ser Gly Gly Ile Val Tyr Met Tyr Pro Glu Glu Thr Asn Lys Tyr
290                 295                 300

Gly Leu Val Ser Ile Asp Gly Asn Asp Val Lys Thr Leu Asp Asp Phe
305                 310                 315                 320

Asn Asn Tyr Ser Ser Glu Ile Asn Lys Ile Ser Pro Thr Ser Ala Asn
                325                 330                 335

Thr Lys Ser Tyr Ser Ala Thr Thr Ser Asp Val Ala Cys Pro Ala Thr
            340                 345                 350

Gly Lys Tyr Trp Ser Ala Ala Thr Glu Leu Pro Pro Thr Pro Asn Gly
            355                 360                 365

Gly Leu Cys Ser Cys Met Asn Ala Ala Asn Ser Cys Val Val Ser Asp
            370                 375                 380

Asp Val Asp Ser Asp Asp Tyr Glu Thr Leu Phe Asn Trp Ile Cys Asn
385                 390                 395                 400

Glu Tyr Asp Cys Ser Gly Ile Ser Ala Asn Gly Thr Ala Gly Lys Tyr
                405                 410                 415
```

-continued

Gly Ala Tyr Ser Phe Cys Thr Pro Lys Glu Gln Leu Ser Phe Val Met
            420                 425                 430

Asn Leu Tyr Tyr Glu Lys Ser Gly Gly Ser Lys Ser Asp Cys Ser Phe
            435                 440                 445

Ser Gly Ser Ala Thr Leu Gln Thr Ala Thr Thr Gln Ala Ser Cys Ser
450                 455                 460

Ser Ala Leu Lys Glu Ile Gly Ser Met Gly Thr Asn Ser Ala Ser Gly
465                 470                 475                 480

Ser Val Asp Leu Gly Ser Gly Thr Glu Ser Ser Thr Ala Ser Ser Asn
                485                 490                 495

Ala Ser Gly Ser Ser Lys Ser Asn Ser Gly Ser Ser Gly Ser Ser
            500                 505                 510

Ser Ser Ser Ser Ser Ser Lys Lys Asn Ala Ala Thr Asn Val Lys
            515                 520                 525

Ala Asn Leu Ala Gln Val Val Phe Thr Ser Ile Ile Ser Leu Phe Ile
530                 535                 540

Ala Ala Gly Val Gly Phe Ala Leu Val
545                 550

<210> SEQ ID NO 14
<211> LENGTH: 550
<212> TYPE: PRT
<213> ORGANISM: Candida albicans

<400> SEQUENCE: 14

Met Tyr Ser Leu Ile Lys Ser Leu Ala Thr Phe Ala Thr Phe Ala Thr
1               5                   10                  15

Leu Phe Ser Leu Thr Leu Ala Lys Phe Glu Ser Ser Thr Pro Pro Val
            20                  25                  30

Glu Val Val Gly Asn Lys Phe Tyr Phe Ser Asn Asn Gly Ser Gln Phe
            35                  40                  45

Leu Ile Arg Gly Ile Ala Tyr Gln Gln Asp Ala Ala Gly Ser Val Ser
        50                  55                  60

Ser Gly Tyr Asp Ala Asp Pro Asn Arg Lys Tyr Asn Asp Pro Leu Ala
65                  70                  75                  80

Asp Arg Asp Ala Cys Lys Arg Asp Val Lys Tyr Phe Lys Glu Ser Asn
                85                  90                  95

Thr Asn Thr Leu Arg Val Tyr Ala Ile Asp Pro Asp Lys Asp His Glu
            100                 105                 110

Glu Cys Met Lys Ile Phe Ser Asp Ala Gly Ile Tyr Ile Val Ala Asp
        115                 120                 125

Leu Ser Glu Pro Thr Val Ser Ile Asn Arg Asn Pro Glu Trp Asn
130                 135                 140

Leu Asp Leu Tyr Lys Arg Tyr Thr Lys Val Ile Asp Lys Met Gln Glu
145                 150                 155                 160

Tyr Ser Asn Val Leu Gly Phe Ala Gly Asn Glu Val Thr Asn Asn
                165                 170                 175

Arg Ser Asn Thr Asp Ala Ser Ala Phe Val Lys Ala Ile Arg Asp
            180                 185                 190

Met Lys Lys Tyr Ile Lys Glu Ser Asp Tyr Arg Gln Ile Pro Val Gly
        195                 200                 205

Ser Ser Asn Asp Asp Glu Glu Ile Arg Val Ala Ile Ala Asp Tyr Phe
210                 215                 220

Ser Cys Gly Ser Leu Asp Asp Arg Ala Asp Phe Phe Gly Ile Asn Met
225                 230                 235                 240

-continued

```
Tyr Glu Trp Cys Gly Lys Ser Thr Phe Glu Thr Ser Gly Tyr Lys Asp
                245                 250                 255

Arg Thr Glu Glu Ile Lys Asn Leu Thr Ile Pro Ala Phe Phe Ser Glu
            260                 265                 270

Tyr Gly Cys Asn Ala Asn Arg Pro Arg Leu Phe Gln Glu Thr Gly Thr
        275                 280                 285

Leu Tyr Ser Asp Lys Met Thr Asp Val Trp Ser Gly Gly Ile Val Tyr
    290                 295                 300

Met Tyr Phe Glu Glu Ala Asn Lys Tyr Gly Leu Val Leu Val Asp Gly
305                 310                 315                 320

Asn Ser Val Lys Thr Leu Ser Asp Tyr Asn Asn Tyr Lys Ser Glu Met
                325                 330                 335

Asn Lys Ile Ser Pro Ser Leu Ala His Thr Ser Thr Leu Ser Ser Ser
            340                 345                 350

Asp Ala Ser Lys Thr Leu Gln Cys Pro Gly Thr Ala Ala Ser Thr Trp
        355                 360                 365

Lys Ala Ala Thr Asn Leu Pro Pro Thr Pro Asp Glu Ser Tyr Cys Asp
    370                 375                 380

Cys Ile Ser Lys Ser Leu Glu Cys Val Val Ala Asp Asp Val Asp Lys
385                 390                 395                 400

Glu Asp Tyr Gly Asp Leu Phe Gly Gln Val Cys Gly Tyr Ile Asp Cys
                405                 410                 415

Ser Ala Ile Ser Ala Asp Gly Ser Lys Gly Glu Tyr Gly Val Ala Ser
            420                 425                 430

Phe Cys Ser Asp Lys Asp Arg Leu Ser Tyr Val Leu Asn Gln Tyr Tyr
        435                 440                 445

Leu Asp Gln Asp Lys Lys Ser Ser Ala Cys Asp Phe Lys Gly Ser Ala
    450                 455                 460

Ser Ile Asn Ser Lys Ala Ser Ala Ser Gly Ser Cys Lys Ala Val Ser
465                 470                 475                 480

Gly Val Ala Thr Gly Lys Ala Ser Ser Gly Gly Ser Ser Lys Ser
                485                 490                 495

Gly Ser Ser Ser Ala Ser Ala Ser Gly Ser Ser Ser Ser Thr Ser
            500                 505                 510

Ser Gly Ser Ser Ser Ser Gly Val Lys Ala Thr Gln Gln Met Ser
        515                 520                 525

Met Val Lys Leu Val Ser Ile Ile Thr Ile Val Thr Ala Phe Val Gly
    530                 535                 540

Gly Met Ser Val Val Phe
545                 550

<210> SEQ ID NO 15
<211> LENGTH: 524
<212> TYPE: PRT
<213> ORGANISM: Saccharomyces cerevisiae

<400> SEQUENCE: 15

Met Gln Leu Ser Lys Ser Ile Leu Leu Ala Ala Leu Ala Ala Thr Pro
1               5                   10                  15

Ser Leu Val Asn Ala Met Leu Pro Ile His Ile Lys Asn Tyr Arg Phe
            20                  25                  30

Ile Lys Pro Ser Ser Ala Thr Asn Ser Glu Ser Asp Asn Glu Val Phe
        35                  40                  45

Phe Val Lys Gly Val Asp Tyr Gln Pro Gly Gly Ser Ser Gly Tyr Asp
    50                  55                  60
```

-continued

```
Ala Asp Ser Asp Thr Asp Ile Leu Ser Asp Pro Glu Val Cys Ala Arg
 65                  70                  75                  80

Asp Ala Tyr Ala Phe Gln Gln Leu Gly Val Asn Thr Val Arg Ile Tyr
                 85                  90                  95

Ser Leu Asn Pro Asp Leu Asn His Asp Lys Cys Met Thr Ile Phe Asn
            100                 105                 110

Asn Ala Gly Ile Tyr Ala Ile Leu Asp Val Asn Ser Gly Asn Tyr Gly
        115                 120                 125

Glu Ser Leu Asn Arg Ala Asp Pro Ser Gly Thr Tyr Asp Ser Leu Tyr
    130                 135                 140

Leu Ser Arg Val Phe Lys Phe Ile Asp Ala Phe Lys Asn Tyr Pro Asn
145                 150                 155                 160

Val Leu Gly Phe Phe Ser Gly Asn Glu Val Ile Asn Asp Gln Ser Asp
                165                 170                 175

Tyr Ala Lys Ile Asp Pro Pro Tyr Ile Arg Ala Val Gln Arg Asp Met
            180                 185                 190

Lys Gln Tyr Ile Ser Lys His Ala Asn Arg Ser Ile Pro Val Gly Tyr
        195                 200                 205

Ser Ala Ala Asp Asn Thr Asp Leu Arg Leu Ala Thr Phe Lys Tyr Leu
    210                 215                 220

Gln Cys Asn Ser Leu Asp Gly Asn Lys Val Asn Asp Asp Leu Asp Ile
225                 230                 235                 240

Ser Lys Ser Asp Phe Phe Gly Leu Asn Thr Tyr Glu Trp Cys Ser Gly
                245                 250                 255

Thr Ser Ser Trp Glu Ser Ser Gly Tyr Asp Lys Leu Asn Ser Thr Phe
            260                 265                 270

Glu Asp Ala Val Ile Pro Leu Ile Phe Ser Glu Tyr Gly Cys Asn Lys
        275                 280                 285

Asn Thr Pro Arg Thr Phe Asp Glu Val Ser Glu Gly Leu Tyr Gly Gly
    290                 295                 300

Leu Lys Asn Val Phe Ser Gly Gly Leu Val Tyr Glu Tyr Thr Glu Glu
305                 310                 315                 320

Ala Asn Asn Tyr Gly Leu Val Lys Leu Asp Asp Ser Gly Ser Leu Thr
                325                 330                 335

Tyr Lys Asp Asp Phe Val Asn Leu Glu Ser Gln Leu Lys Asn Val Ser
            340                 345                 350

Leu Pro Thr Thr Lys Glu Ser Glu Ile Ser Ser Asp Ser Ile Tyr Lys
        355                 360                 365

Cys Asp Asn Ser Ala Ile Thr Asn Ile Tyr Ser Gly Phe Gly Thr Asn
    370                 375                 380

Asn Phe Thr Leu Pro Ser Gln Pro Ala Glu Ile Ala Asn Met Ile Glu
385                 390                 395                 400

Tyr Gly Val Asn Gly Thr Asn Thr Gly Lys Ile Leu Thr Asp Tyr Ala
                405                 410                 415

Val Pro Thr Thr Phe Asn Tyr Thr Ile Lys Asn Asn Lys Asp Asp Thr
            420                 425                 430

Ile Ser Ala Thr Ile Ser Tyr Asp Lys Ala Asn Ser Leu Asn Glu Leu
        435                 440                 445

Asp Val Thr Ala Thr Val Ala Lys Ser Ala Ser Thr Ser Gln Ser
    450                 455                 460

Ser Ser Arg Ser Leu Thr Ser Ser Thr Ser Pro Ser Ser Thr Gly
465                 470                 475                 480
```

Ser Ser Ser Ser Thr Gly Ser Ser Ala Ser Ser Ser Lys Ser
            485                 490                 495

Lys Gly Val Gly Asn Ile Val Asn Val Ser Phe Ser Gln Ser Gly Tyr
                500                 505                 510

Leu Ala Leu Phe Ala Gly Leu Ile Ser Ala Leu Leu
            515                 520

<210> SEQ ID NO 16
<211> LENGTH: 471
<212> TYPE: PRT
<213> ORGANISM: Saccharomyces cerevisiae

<400> SEQUENCE: 16

Met Met Val Phe Ser Ser Thr Phe Ile Phe Leu Ile Leu Glu Leu Val
 1               5                  10                  15

Val Leu Cys Glu Ala Ser Val His Thr Ile Gln Ile Lys Asp Lys His
                20                  25                  30

Phe Val Asp Thr Val Thr Gly Lys Pro Phe Phe Ile Lys Gly Val Asp
            35                  40                  45

Tyr Gln Pro Gly Gly Ser Ser Asp Val Ser Glu Lys Gln Asp Pro Leu
        50                  55                  60

Ser Asn Pro Asp Ala Cys Ala Arg Asp Ile Leu Leu Phe Gln Glu Leu
65                  70                  75                  80

Gly Ile Asn Thr Val Arg Ile Tyr Ser Ile Asn Pro Asp Leu Asn His
                85                  90                  95

Asp Ala Cys Met Thr Met Leu Ala Met Ala Gly Ile Tyr Leu Ile Leu
                100                 105                 110

Asp Val Asn Ser Pro Leu Gln Asn Gln His Leu Asn Arg Tyr Glu Pro
            115                 120                 125

Trp Thr Thr Tyr Asn Glu Val Tyr Leu Glu His Val Phe Lys Val Val
130                 135                 140

Glu Gln Phe Ser His Tyr Asn Asn Thr Leu Gly Phe Phe Ala Gly Asn
145                 150                 155                 160

Glu Ile Val Asn Asp Lys Arg Ser Ala Gln Tyr Ser Pro Ala Tyr Val
                165                 170                 175

Lys Glu Leu Ile Gly Thr Met Lys Asn Tyr Ile Ser Ala His Ser Pro
            180                 185                 190

Arg Thr Ile Pro Val Gly Tyr Ser Ala Ala Asp Asp Leu Asn Tyr Arg
        195                 200                 205

Val Ser Leu Ser Glu Tyr Leu Glu Cys Lys Asp Asp Lys Pro Glu
210                 215                 220

Asn Ser Val Asp Phe Tyr Gly Val Asn Ser Tyr Gln Trp Cys Gly Gln
225                 230                 235                 240

Gln Thr Met Gln Thr Ser Gly Tyr Asp Thr Leu Val Asp Ala Tyr Arg
                245                 250                 255

Ser Tyr Ser Lys Pro Val Phe Phe Ser Glu Phe Gly Cys Asn Lys Val
            260                 265                 270

Leu Pro Arg Gln Phe Gln Glu Ile Gly Tyr Leu Phe Ser Glu Glu Met
        275                 280                 285

Tyr Ser Val Phe Cys Gly Gly Leu Val Tyr Glu Phe Ser Gln Glu Asp
    290                 295                 300

Asn Asn Tyr Gly Leu Val Glu Tyr Gln Glu Asp Ser Val Gln Leu
305                 310                 315                 320

Leu Ala Asp Phe Glu Lys Leu Lys Ser His Tyr Gln Asn Ile Glu Phe
                325                 330                 335

```
Pro Ser Met Lys Thr Leu Lys Glu Thr Val Gln Met Glu Glu Thr Pro
            340                 345                 350

Ser Cys Ala Glu Asp Tyr Glu Asn Leu Lys Ile Glu Ser Lys Ile Ala
            355                 360                 365

Lys Asn Leu Gly Ser Ser Leu Ile Lys Lys Gly Val Lys Val Glu Lys
            370                 375                 380

Gly Lys Tyr Ile Asp Ile His Glu Asp Gln Leu Ser Thr Asn Val Thr
385                 390                 395                 400

Ile Leu Asp Lys His Gly Asp Arg Trp Asn Gly Pro Lys Lys Ile Glu
                405                 410                 415

Ile Arg Gln Ser Leu Thr Leu Ala Asp Leu Glu Gly Glu Glu Gln Glu
            420                 425                 430

Asp Ala Asp Glu Asp Lys Asp Asp Leu Lys Arg Lys His Arg Asn Ser
            435                 440                 445

Ala Ser Ile Ser Gly Pro Leu Leu Pro Leu Gly Leu Cys Leu Leu Phe
            450                 455                 460

Phe Thr Phe Ser Leu Phe Phe
465                 470

<210> SEQ ID NO 17
<211> LENGTH: 484
<212> TYPE: PRT
<213> ORGANISM: Saccharomyces cerevisiae

<400> SEQUENCE: 17

Met Leu Leu Arg Ser Leu Thr Ser Ala Phe Val Leu Ser Ala Gly Leu
1               5                   10                  15

Ala Gln Ala Ala Ser Ser Ser Asn Ser Ser Thr Pro Ser Ile Glu Ile
            20                  25                  30

Lys Gly Asn Ala Phe Phe Asn Ser Glu Ser Gly Glu Arg Phe Tyr Ile
            35                  40                  45

Arg Gly Val Asp Tyr Gln Pro Gly Gly Ser Ser Asn Leu Thr Asp Pro
        50                  55                  60

Leu Ala Asp Ala Ser Val Cys Asp Arg Asp Val Pro Val Leu Lys Asp
65                  70                  75                  80

Leu Gly Ile Asn Thr Val Arg Val Tyr Thr Val Asp Asn Ser Gln Asp
                85                  90                  95

His Ser His Cys Met Lys Leu Leu Gln Glu Asn Gly Ile Tyr Leu Ile
                100                 105                 110

Leu Asp Val Asn Thr Pro Thr Ser Ala Ile Ser Arg Tyr Asp Pro Ala
            115                 120                 125

Cys Ser Tyr Asn Ala Asp Tyr Leu Gln Asn Val Phe Ala Thr Ile Asp
        130                 135                 140

Thr Phe Ala Asp Tyr Asp Asn Val Leu Gly Phe Phe Ala Gly Asn Glu
145                 150                 155                 160

Val Ile Asn Ser Val Asn Thr Asn Thr Ala Thr Tyr Val Lys Ala
                165                 170                 175

Val Val Arg Asp Met Lys Lys Tyr Ile Lys Ala Arg Lys Tyr Arg Gln
            180                 185                 190

Ile Pro Val Gly Tyr Ser Ala Ala Asp Ile Val Ala Asn Arg Gln Leu
        195                 200                 205

Ala Ala Glu Tyr Phe Asn Cys Gly Asp Glu Ala Asp Ala Arg Ile Asp
            210                 215                 220

Met Phe Gly Val Asn Asp Tyr Ser Trp Cys Gly Glu Ser Ser Phe Val
225                 230                 235                 240
```

-continued

```
Val Ser Gly Tyr Ser Thr Lys Met Lys Leu Tyr Gln Asp Tyr Ser Val
                245                 250                 255

Pro Val Phe Leu Ser Glu Phe Gly Cys Asn Gln Val Lys Ser Ser Arg
            260                 265                 270

Pro Phe Thr Glu Ile Glu Ala Ile Tyr Ser Thr Gln Met Ser Ser Val
        275                 280                 285

Phe Ser Gly Gly Leu Val Tyr Glu Tyr Ser Asn Glu Thr Asn Asn Tyr
    290                 295                 300

Gly Leu Val Gln Ile Asp Gly Asp Lys Val Thr Lys Leu Thr Asp Phe
305                 310                 315                 320

Glu Asn Leu Lys Asn Glu Tyr Ser Lys Val Ser Asn Pro Glu Gly Asn
                325                 330                 335

Gly Gly Tyr Ser Thr Ser Asn Asn Tyr Ser Thr Cys Pro Asp Tyr Glu
            340                 345                 350

Lys Gly Val Trp Glu Ala Asn Asn Thr Leu Pro Ala Met Pro Ser Ala
        355                 360                 365

Ala Ser Ala Tyr Phe Thr Ser Gly Ala Gly Ser Pro Met Gly Thr Gly
    370                 375                 380

Ile Ala Thr Gln Gln Ser Cys Asp Ala Lys Asp Asp Asp Glu Glu
385                 390                 395                 400

Asp Asp Asp Thr Ser Ser Ser Ser Ser Ser Ser Ser Ser Ser Ser Ser
                405                 410                 415

Ser Ala Ser Ser Ser Ser Glu Ser Ser Ser Ser Thr Ser Lys Ala Ser
            420                 425                 430

Ser Ser Ser Pro Ser Ala Ser Glu Thr Ser Leu Leu Lys Ser Ala Ala
        435                 440                 445

Ser Ala Thr Ser Ser Ser Gln Ser Ser Ser Lys Ser Lys Gly Ala Ala
    450                 455                 460

Gly Ile Ile Glu Ile Pro Leu Ile Phe Arg Ala Leu Ala Glu Leu Tyr
465                 470                 475                 480

Asn Leu Val Leu
```

<210> SEQ ID NO 18
<211> LENGTH: 555
<212> TYPE: PRT
<213> ORGANISM: Saccharomyces cerevisiae

<400> SEQUENCE: 18

```
Met Asn Lys Lys Gln Asn Phe Tyr Ala Ala Ile Ile Val Ala Ile Phe
1               5                   10                  15

Leu Cys Leu Gln Leu Ser His Gly Ser Ser Gly Val Ser Phe Glu Lys
            20                  25                  30

Thr Pro Ala Ile Lys Ile Val Gly Asn Lys Phe Phe Asp Ser Glu Ser
        35                  40                  45

Gly Glu Gln Phe Phe Ile Lys Gly Ile Ala Tyr Gln Leu Gln Arg Ser
    50                  55                  60

Glu Glu Glu Leu Ser Asn Ala Asn Gly Ala Phe Glu Thr Ser Tyr Ile
65                  70                  75                  80

Asp Ala Leu Ala Asp Pro Lys Ile Cys Leu Arg Asp Ile Pro Phe Leu
                85                  90                  95

Lys Met Leu Gly Val Asn Thr Leu Arg Val Tyr Ala Ile Asp Pro Thr
            100                 105                 110

Lys Ser His Asp Ile Cys Met Glu Ala Leu Ser Ala Glu Gly Met Tyr
        115                 120                 125
```

-continued

```
Val Leu Leu Asp Leu Ser Glu Pro Asp Ile Ser Ile Asn Arg Glu Asn
    130                 135                 140

Pro Ser Trp Asp Val His Ile Phe Glu Arg Tyr Lys Ser Val Ile Asp
145                 150                 155                 160

Ala Met Ser Ser Phe Pro Asn Leu Leu Gly Tyr Phe Ala Gly Asn Glu
                165                 170                 175

Val Thr Asn Asp His Thr Asn Thr Phe Ala Ser Pro Phe Val Lys Ala
            180                 185                 190

Ala Ile Arg Asp Ala Lys Glu Tyr Ile Ser His Ser Asn His Arg Lys
        195                 200                 205

Ile Pro Val Gly Tyr Ser Thr Asn Asp Asp Ala Met Thr Arg Asp Asn
    210                 215                 220

Leu Ala Arg Tyr Phe Val Cys Gly Asp Val Lys Ala Asp Phe Tyr Gly
225                 230                 235                 240

Ile Asn Met Tyr Glu Trp Cys Gly Tyr Ser Thr Tyr Gly Thr Ser Gly
                245                 250                 255

Tyr Arg Glu Arg Thr Lys Glu Phe Glu Gly Tyr Pro Ile Pro Val Phe
            260                 265                 270

Phe Ser Glu Phe Gly Cys Asn Leu Val Arg Pro Arg Pro Phe Thr Glu
        275                 280                 285

Val Ser Ala Leu Tyr Gly Asn Lys Met Ser Ser Val Trp Ser Gly Gly
    290                 295                 300

Leu Ala Tyr Met Tyr Phe Glu Glu Asn Glu Tyr Gly Val Val Lys
305                 310                 315                 320

Ile Asn Asp Asn Asp Gly Val Asp Ile Leu Pro Asp Phe Lys Asn Leu
                325                 330                 335

Lys Lys Glu Phe Ala Lys Ala Asp Pro Lys Gly Ile Thr Glu Glu Glu
            340                 345                 350

Tyr Leu Thr Ala Lys Glu Pro Thr Glu Val Glu Ser Val Glu Cys Pro
        355                 360                 365

His Ile Ala Val Gly Val Trp Glu Ala Asn Glu Lys Leu Pro Glu Thr
    370                 375                 380

Pro Asp Arg Ser Lys Cys Ala Cys Leu Asp Glu Ile Leu Pro Cys Glu
385                 390                 395                 400

Ile Val Pro Phe Gly Ala Glu Ser Gly Lys Tyr Glu Glu Tyr Phe Ser
                405                 410                 415

Tyr Leu Cys Ser Lys Val Asp Cys Ser Asp Ile Leu Ala Asn Gly Lys
            420                 425                 430

Thr Gly Glu Tyr Gly Glu Phe Ser Asp Cys Ser Val Glu Gln Lys Leu
        435                 440                 445

Ser Leu Gln Leu Ser Lys Leu Tyr Cys Lys Ile Gly Ala Asn Asp Arg
    450                 455                 460

His Cys Pro Leu Asn Asp Lys Asn Val Tyr Phe Asn Leu Glu Ser Leu
465                 470                 475                 480

Gln Pro Leu Thr Ser Glu Ser Ile Cys Lys Asn Val Phe Asp Ser Ile
                485                 490                 495

Arg Asn Ile Thr Tyr Asn His Gly Asp Tyr Ser Lys Ser Asn Pro Ser
            500                 505                 510

Arg Ser Lys Glu Ser Leu Asn Val Lys Tyr Pro Ser Ser Glu Glu Arg
        515                 520                 525
```

-continued

```
Glu Asn Asp Gly Thr Ile Ala Phe Lys Thr Ser Gly Phe Val Ile Leu
            530                 535                 540

Leu Ile Ser Met Ile Ala Ala Gly Ile Leu Leu
545                 550                 555

<210> SEQ ID NO 19
<211> LENGTH: 552
<212> TYPE: PRT
<213> ORGANISM: Candida albicans

<400> SEQUENCE: 19

Met Tyr Ser Leu Ile Lys Ser Leu Ala Thr Phe Ala Thr Phe Ala Thr
  1               5                  10                  15

Leu Phe Ser Leu Thr Leu Ala Lys Phe Glu Ser Ser Thr Pro Pro Val
               20                  25                  30

Glu Val Val Gly Asn Lys Phe Tyr Phe Ser Asn Asn Gly Ser Gln Phe
           35                  40                  45

Leu Ile Arg Gly Ile Ala Tyr Gln Gln Asp Ala Ala Gly Ser Val Ser
       50                  55                  60

Ser Gly Tyr Asp Ala Asp Pro Asn Arg Lys Tyr Asn Asp Pro Leu Ala
 65                  70                  75                  80

Asp Arg Asp Ala Cys Lys Arg Asp Val Lys Tyr Phe Lys Glu Ser Asn
                 85                  90                  95

Thr Asn Thr Leu Arg Val Tyr Ala Ile Asp Pro Asp Lys Asp His Glu
            100                 105                 110

Glu Cys Met Lys Ile Phe Ser Asp Ala Gly Ile Tyr Ile Val Ala Asp
            115                 120                 125

Leu Ser Glu Pro Thr Val Ser Ile Asn Arg Asn Asn Pro Glu Trp Asn
145                 135                 140

Leu Asp Leu Tyr Lys Arg Tyr Thr Lys Val Ile Asp Lys Met Gln Glu
145                 150                 155                 160

Tyr Ser Asn Val Leu Gly Phe Phe Ala Gly Asn Glu Val Thr Asn Asn
                165                 170                 175

Arg Ser Asn Thr Asp Ala Ser Ala Phe Val Lys Ala Ile Arg Asp
            180                 185                 190

Met Lys Lys Tyr Ile Lys Glu Ser Asp Tyr Arg Gln Ile Pro Val Gly
            195                 200                 205

Tyr Ser Ser Asn Asp Asp Glu Glu Ile Arg Val Ala Ile Ala Asp Tyr
210                 215                 220

Phe Ser Cys Gly Ser Leu Asp Asp Arg Ala Asp Gly Phe Gly Ile
225                 230                 235                 240

Asn Met Tyr Glu Trp Cys Gly Lys Ser Thr Phe Glu Thr Ser Gly Tyr
                245                 250                 255

Lys Asp Arg Thr Glu Glu Ile Lys Asn Leu Thr Ile Pro Ala Phe Phe
            260                 265                 270

Ser Glu Tyr Gly Cys Asn Ala Asn Arg Pro Arg Leu Phe Gln Glu Ile
            275                 280                 285

Gly Thr Leu Tyr Ser Asp Lys Met Thr Asp Val Trp Ser Gly Gly Ile
            290                 295                 300

Val Tyr Met Tyr Phe Glu Glu Ala Asn Lys Tyr Gly Leu Val Leu Val
305                 310                 315                 320

Asp Gly Asn Ser Val Lys Thr Leu Ser Asp Tyr Asn Asn Tyr Lys Ser
                325                 330                 335

Glu Met Asn Lys Ile Ser Pro Ser Leu Ala His Thr Ser Thr Leu Ser
            340                 345                 350
```

```
Ser Ser Asp Ala Ser Lys Thr Leu Gln Cys Pro Gly Thr Ala Ala Ser
        355                 360                 365

Thr Trp Lys Ala Ala Thr Asn Leu Pro Pro Thr Pro Asp Glu Ser Tyr
    370                 375                 380

Cys Asp Cys Ile Ser Lys Ser Leu Glu Cys Val Val Ala Asp Asp Val
385                 390                 395                 400

Asp Lys Glu Asp Tyr Gly Asp Leu Phe Gly Gln Val Cys Gly Tyr Ile
                405                 410                 415

Asp Cys Ser Ala Ile Ser Ala Asp Gly Ser Lys Gly Glu Tyr Gly Val
                420                 425                 430

Ala Ser Phe Cys Ser Asp Lys Asp Arg Leu Ser Tyr Val Leu Asn Gln
        435                 440                 445

Tyr Tyr Leu Asp Gln Asp Lys Lys Ser Ser Ala Cys Asp Phe Lys Gly
450                 455                 460

Ser Ala Ser Ile Asn Ser Lys Ala Ser Ala Ser Gly Ser Cys Lys Ala
465                 470                 475                 480

Val Ser Gly Val Ala Thr Gly Lys Ala Ser Ser Ser Gly Gly Ser Ser
                485                 490                 495

Lys Ser Gly Ser Ser Ala Ser Ala Ser Gly Ser Ser Ser Ser Ser Ser
                500                 505                 510

Thr Ser Ser Gly Ser Ser Ser Ser Gly Val Lys Ala Thr Gln Gln
        515                 520                 525

Met Ser Met Val Lys Leu Val Ser Ile Ile Thr Ile Val Thr Ala Phe
        530                 535                 540

Val Gly Gly Met Ser Val Val Phe
545                 550

<210> SEQ ID NO 20
<211> LENGTH: 20
<212> TYPE: PRT
<213> ORGANISM: Aspergillus fumigatus

<400> SEQUENCE: 20

Asp Val Thr Pro Ile Thr Val Lys Gly Asn Ala Phe Phe Lys Gly
1               5                   10                  15

Asp Glu Arg Phe Tyr
                20

<210> SEQ ID NO 21
<211> LENGTH: 13
<212> TYPE: PRT
<213> ORGANISM: Aspergillus fumigatus

<400> SEQUENCE: 21

Asp Ala Pro Asn Trp Asp Val Asp Asn Asp Ala Leu Pro
1               5                   10
```